(12) United States Patent
Bachmann

(10) Patent No.: US 9,072,778 B2
(45) Date of Patent: Jul. 7, 2015

(54) TREATMENT REGIMEN FOR N-MYC, C-MYC, AND L-MYC AMPLIFIED AND OVEREXPRESSED TUMORS

(75) Inventor: Andre S. Bachmann, Waipahu, HI (US)

(73) Assignee: UNIVERSITY OF HAWAII, Honolulu, HI (US)

( * ) Notice: Subject to any disclaimer, the term of this patent is extended or adjusted under 35 U.S.C. 154(b) by 1287 days.

(21) Appl. No.: 12/158,661

(22) PCT Filed: Dec. 20, 2006

(86) PCT No.: PCT/US2006/048412
§ 371 (c)(1),
(2), (4) Date: Oct. 13, 2008

(87) PCT Pub. No.: WO2007/075673
PCT Pub. Date: Jul. 5, 2007

(65) Prior Publication Data
US 2009/0203784 A1    Aug. 13, 2009

Related U.S. Application Data

(60) Provisional application No. 60/752,414, filed on Dec. 20, 2005.

(51) Int. Cl.
| | |
|---|---|
| A61K 31/198 | (2006.01) |
| A61K 31/365 | (2006.01) |
| A61K 31/203 | (2006.01) |
| A61K 45/06 | (2006.01) |
| A61K 31/167 | (2006.01) |

(52) U.S. Cl.
CPC ............... *A61K 45/06* (2013.01); *A61K 31/365* (2013.01); *A61K 31/167* (2013.01); *A61K 31/198* (2013.01); *A61K 31/203* (2013.01)

(58) Field of Classification Search
CPC .................................................. A61K 31/198
See application file for complete search history.

(56) References Cited

U.S. PATENT DOCUMENTS

| 4,499,072 A * | 2/1985 | Sunkara et al. ............... 424/85.7 |
| 6,573,290 B1 | 6/2003 | Love |
| 2002/0045663 A1* | 4/2002 | Levenson et al. ............. 514/564 |
| 2002/0137797 A1* | 9/2002 | Meyskens et al. ............ 514/564 |

FOREIGN PATENT DOCUMENTS

WO    WO 2004/018001    3/2004

OTHER PUBLICATIONS

Bartholeyns et al. Cancer Research, 1981, vol. 41, pp. 5158-5161.*
Heston et al. Cancer Letters, 1982, vol. 16, No. 1, pp. 71-79 (Abstract attached).*
Prakash et al. Cancer Research, 1983, vol. 43, pp. 3192-3196.*
Verma et al. Carcinogenesis, 1986, vol. 7, No. 6, pp. 1019-1023 (Abstract attached).*
Shrestha et al. Surgery Today, 1992, vol. 22, No. 2, pp. 137-142 (Abstract attached).*
Kurihara et al. Neurol. Med. Chir. (Tokyo), 1995, vol. 35, pp. 215-220.*
Quemener et al. Anticancer Research, 1994, vol. 14, No. 2A, pp. 443-448 (Abstract attached).*
Leveque et al. Anticancer Research, 1998, vol. 18, No. 4A, pp. 2663-2668 (Abstract attached).*
Shrestha et al. Gan. No. Rinsho. Japan Journal of Cancer Clinics, 1987, vol. 33, No. 2, pp. 179-183 (Abstract attached).*
Lovat et al. Int. J. Cancer, 2000, vol. 88, pp. 977-985.*
Kim. Yengnam Univ. J. Med., 1997, vol. 14, No. 1, pp. 67-76 (Abstract attached).*
Yamaguchi et al. Int. J. Clin. Onco., 2001, vol. 6, No. 5, pp. 259-261 (Abstract Attached).*
Lovat et al. Int. J. Cancer, 2000, vol. 88, No. 6, pp. 977-985 (Abstract Attached).*
Pendyala et al. Cancer Epidemiol Biomarkers Prev 1993;2:235-241.*
Wallick, et al. 2005. "Key role for $p27^{Kip1}$ retinoblastoma protein Rb, and MYCN in polyamine inhibitor-induced $G_1$ call cycle arrest in MYCN-amplified human neuroblastoma cells." *Oncogene* 24: 5606-5618.
Bachmann, et al. 2004. "The role of the polyamines in human cancer: prospects for drug combination therapies." *Hawaii Medical Journal* 63(12):371-374.
Bachrach, U. 2004. "Polyamines and cancer: Minireview article." *Amino Acids* 26:307-309.
Bachrach, et al. 2001. "Polyamines: New cues in cellular signal Transduction." *News Physiol Sci* 16:106-109.
Bacchi, et al. 2002. "Novel synthetic polyamines are effective in the treatment of experimental microsporidiosis, an opportunistic AIDS-associated infection." *Antimicrobial Agents and Chemotherapy* 46(1):55-61.
Ben-Yosef, et al. 1998. "Involvement of myc targets in c-myc and N-myc induced human tumors." *Oncogene* 17:165-171.
Brodeur, Garrett M. 2003. "neuroblastoma:Biological insights into a clinical enigma." *Nature Reviews Cancer* 3:203-216.
Brodeur, et al. 1984. "Amplification of N-myc in untreated human neuroblastomas correlates with advanced disease stage." *Science* 224(4653):1121-1124.
Carbone, et al. 2001. "Phase I chemoprevention study of difluoromethylornithine in subjects with organ transplants." *Cancer Epidemiology, Biomarkers, & Prevention* 10:657-661.

(Continued)

*Primary Examiner* — James D Anderson
(74) *Attorney, Agent, or Firm* — Davis Wright Tremaine LLP

(57) ABSTRACT

The present invention relates to methods and compositions for treating diseases. More specifically, the present invention relates to the administration of multiple drugs as part of a treatment of disease. Specific embodiments of the invention relate to a treatment regimen for neuroblastomas and other N-MYC, c-MYC, and L-MYC amplified and overexpressed tumors, comprising administering multiple therapeutic compounds like DFMO, SAM486A, a verinoid and a cytotoxic drug and placing the patient on a low polyamine diet and/or providing the patient with a polyamine limiting dietary supplement.

6 Claims, 10 Drawing Sheets

(56) References Cited

OTHER PUBLICATIONS

Chen, et al. 2003. "The role of mitogen-activated protein kinase activation in determining cellular outcomes in polyamine analogue-treated human melanoma cells." *Cancer Research* 63:3619-3625.
Davidson, et al. 1999. "Clinical aspects of cell death in breast cancer: the polyamine pathway as a new target for treatment." *Endocrine-Related Cancer* 6:69-73.
Dawson, et al. 1987 "Inhibition by retinaoids of anthralin-induced mouse epidermal ornithine decarboyylase activity and anthralin-promoted skin tumor formation[1]." *Cancer Research* 47:6210-6215.
Dawson, et al. 2001. "Retinoic acid (RA) receptor transcriptional activation correlates with inhibition of 12-O-tetradecanoylphorbol-13-acetate-induced ornithine decarboxylase (ODC) activity by retinoids: a potential role for trans-RA-induced ZBP0-89 in ODC inhibition." *Int. J. Cancer* 91:8-21.
Dorhout, et al. 1995. "In vivo effects of 4-amidinoindan-1-one 2'-amidinohydrazone (CGP 48664A) and α-difluoromethylornithine (DFMO) on L1210 growth, cell-cycle phase distribution and polyamine contents." *International Journal of Cancer* 62:738-742.
Eskens, et al. 2000. "Phase I and pharmacological study of weekly administration of the polyamine synthesis inhibitor SAM 486A (CGP 48 664) in patients with solid tumors." *Clinical Cancer Research* 6:1736-1743.
Fabian, et al. 2002. "A phase II breat cancer chemoprevention trial of oral α-difluoromethylornithine: Breat tissue, imaging, and serum and urine biomarkers[1]." *Clinical Cancer Research* 8:3105-3117.
Fingl, et al. 1975. "General Principles." *The Pharmacological Basis of Therapeutics* 1:1-46.
Galderisi, et al. 1999. "Differentiation and apoptosis of neuroblastoma cells: Role of N-myc gene product." *Journal of Cellular Biochemistry* 73:97-105.
Galderisi, et al. 2003. "Cell cycle regulation and neural differentiation." *Oncogene* 22:5208-5219.
Hahm, et al. 2001. "Combination of standard cytotoxic agents with polyamine analogues in the treatment of breast cancer cell lines." *Clinical Cancer Research* 7:391-399.
Heby, et al. 1990. "Molecular genetics of polyamine synthesis in eukaryotic cells." *Trends Biochem Sci* 15:153-158.
Heby, Olle 1981. "Role of polyamines in the control of cell proliferation and differentiation." *Differentiation* 19:1-20.
Heby, et al. 2003. "Polyamine biosynthetic enzymes as drug targets in parasitic protozoa." *Biochemical Society Transactions* 31(2):415-419.
Hopkins-Donaldson, et al. 2002. "Doxorubicin-induced death in neuroblastoma does not involve death receptors in S-type cells and is caspase-independent in N-type cells." *Oncogene* 21: 6132-6137.
Huang, et al. 2003. "A novel polyamine analog inhibits growth and induces apoptosis in human breast cancer cells." *Clinical Cancer Research* 9:2769-2777.
Kramer, et al. 2001. "Polyamine depletion in human melanoma cells leads to $G_1$ arrest associated with induction of $p21^{WAF1/CIP1/SDI1}$, changes in the expression of p21-regulated genes, and a senecence-like phenotype[1]." *Cancer Research* 61:7754-7762.
Kramer, et al. 1989. "Cellular characterization of a new irreversible inhibitor of S-adenosylmethionine decarboxylase and its use in determining the relative abilities of individual polyamines to sustain growth and viability of L1210 cells." *Biochem J.* 259:325-331.
Levin, et al. 2003. "Phase III randomized study of postradiotherapy chemotherapy with combination α-difluoromethylornithine-PCV versus PCV for anaplastic gliomas[1]." *Clinical Cancer Research* 9:981-990.
Levin, et al. 2000. "Phase III randomized study of postradiotherapy chemotherapy with α-difluoromethylornithine-procarbazine, N-(2-cloroethyl)-N'-cyclohexyl-N-nitrosurea, Vincristine (DFMO-PCV) versus PCV for glioblastoma multiforme." *Clinical Cancer Research* 6:3878-3884.
Lu, et al. 2003. "The MYCN oncoprotein as a drug development target." *Cancer Letters* 197:125-130.
Lutz, et al. 1996. "Conditional expression of N-myc in human neuroblastoma cells increases expression of α-prothymosin and ornithine decarboxylase and accelerates progression into S-phase early after mitogenic stimulation of quiescent cells." *Oncogene* 13:803-812.
Matsuo, et al. 1998. "$p27^{Kip1}$: a key mediator of retinoic acid induced growth arrest in the SMS-KCNR human neuroblastoma cell line." *Oncogene* 16:3337-3343.
McCann, et al. 1992. "Ornithine decarboxylase as an enzyme target for therapy." *Pharmac. Ther.* 54:195-215.
McKenzie, et al. 2003. "$p21^{Waf1/Cip1}$ dysfunction in neuroblastoma: A novel mechanism of attenuating $G_0$-$G_1$ cell cycle arrest." *Cancer Research* 6: 3840-3844.
Meyskens, et al. 1999. "Development of difluoromethylornithine (DFMO) as a chemoprevention agent[1]." *Clinical Cancer Research* 5:945-951.
Milovic, et al. 2003. "Polyamines and colon cancer." *Biochemical Society Transactions* 31(2):381-383.
Moon, et al. 1994. "Chemoprevention of OH-BBN-induced bladder cancer in mice by oltipraz, alone and in combination with 4-HPR and DFMO." *Anticancer Research* 14: 5-12.
Nakamura, et al. 2003. "Retinoic acid decreases targeting of p27 for degradation via an N-myc-dependent decrease in p27 phosphorylation and an N-myc-independent decrease in Skp2." *Cell Death and Differentiation* 10:230-239.
Nishioka, et al. 1996. "Clinical studies of polyamine and their antimetabolites." *Polyamines in Cancer: Basic Mechanisms and Clinical Approaches* 11:251-278.
Oredsson, S. M. 2003. "Polyamine dependence of normal cell-cycle progression." *Biochemical Society Transactions* 31(2):366-370.
Paridaens, et al. 2000. "A phase I study of a new polyamine biosynthesis inhibitor, SAM486A, in cancer patients with solid tumours." *British Journal of Cancer* 83:594-601.
Pegg, Anthony E. 1988. "Polyamine metabolism and its importance in neoplastic growth and as a target for chemotherapy." *Cancer Research* 48:759-774.
Pegg, Anthony E. 1986. "Recent advances in the biochemistry of polyamines in eukaryotes." *Biochem. J.* 234:249-262.
Pegg, et al. 1998. "S-adenosylmethionine decarboxylase: structure, function and regulation by polyamines." *Biochemical Society Transactions* 26:580-586.
Pless, et al. 2004. "Clinical efficacy, tolerability, and safety of SAM486A, a novel polyamine biosynthesis inhibitor, in patients with relapsed or refractory non-Hodgkin's lymphoma: Results from a phase II multicenter study." *Clinical Cancer Research* 10:1299-1305.
Pines, Jonathon 1994. "The cell cycle kinases." *Seminars in Cancer Biology* 5:305-313.
Porter, et al. (1992) "Polyamine inhibitors and analogues as potential anticancer agents." *Polyamines in the Gastointestinal Tract* 31:301-22.
Ray, et al. 1999. "Polyamine depletion arrests cell cycle and induces inhibitors p21Waf1/Cip1, p27Kip1, and p53 in IEC-6 cells." *Am J Physiol Cell Physiol* 276:684-691.
Regenass, et al. 1994. "CGP 48664,a new S-adenosylmethionine decarboxylase inhibitor with broad spectrum antiproliferative and antitumor activity." *Cancer Research* 54:3210-3217.
Reynolds, et al. 2003. "Retinoid therapy of high-risk neuroblastoma." *Cancer Letters* 197:185-192.
Russell, Diane H. 1971. "Increased polyamine concentrations in the urine of human cancer patients." *Nature New Biology* 233:144-145.
Schedin, et al. 1995. "Treatment with chemoprotective agents, difluoromethylornithine and retinyl acetate, results in altered mammary extracellular matrix." *Carcinogenesis* 16 (8): 1787-1794.
Schipper, et al. 2003. "Polyamines and prostatic cancer." *Biochemical Society Transactions* 31(2):375-380.
Seeger, et al. 1985. "Association of multiple copies of the N-myc oncogene with rapid progression of neuroblastomas." *N Engl J Med* 313(18):1111-1116.
Seiler, Nikolaus 2003. "Thirty years of polyamine-related approaches to cancer therapy. Retrospect and prospect. Part 1. Selective enzyme inhibitors." *Current Drug Targets* 4:537-564.

(56) References Cited

OTHER PUBLICATIONS

Seiler, Nikolaus 2003. "Thirty years of polyamine-related approaches to cancer therapy. Retrospect and prospect. Part 2. Structural analogues and derivatives." *Current Drug Targets* 4:565-585.

Singh, et al. 2001. "Activation of caspase-3 activity and apoptosis in MDA-MB-468 cells by Nω-hydroxy-L-arginine, an inhibitor of arginase, is not solely dependent on reduction in intracellular polyamines." *Carcinogenesis* 22(11):1863-1869.

Siu, et al. 2002. "A phase I and pharmacokinetic study of SAM486A, a novel polyamine biosynthesis inhibitor, administered on a daily-times-five every-three-week schedule in patients with advanced solid malignancies." *Clinical Cancer Research* 8:2157-2166.

Svensson, et al. 1997. "CGP 48664, a potent and specific S-adenosylmethionine decarboxylase inhibitor: effects on regulation and stability of the enzyme." *Biochem. J.* 322:297-302.

Tabib, et al. 1994. "Activation of the proto-oncogene c-myc and c-fos by c-ras: Involvement of polyamines." *Biochemical Biophysical Research Communications* 202(2):720-727.

Tabor, et al. 1984. "Polyamines." *Ann. Rev. Biochem.* 53:749-790.

Thomas, et al. 2003. "Polyamine metabolism and cancer." *J. Cell. Mol. Med.* 7(2):113-126.

Thomas, et al. 2001. "Polyamines in cell growth and cell death: molecular mechanisms and therapeutic applications." *Cell. Mol. Life Sci.* 58:244-258.

Tuthill, et al. 2003. "Targeting oncogene expression in a childhood cancer." *Hawaii Med J* 62:224-225.

Van Zuylen, et al. 2004. "Phase I and pharmacokinetic study of the polyamine synthesis inhibitor SAM486A in combination with 5-fluorouracil/leucovorin in metastatic colorectal cancer." *Cancer Research* 10:1949-1955.

Wallace, et al. 2003. "A perspective of polyamine metabolism." *Biochem. J.* 376:1-14.

Woster, Patrick M. 2006. "Polyamine structure and synthetic analogs." *Polyamine Cell Signaling: Physiology, Pharmacology, and Cancer Research* 3-24.

Zhang, et al. 2004. "Akt kinase activation blocks apoptosis in intestinal epithelial cells by inhibiting caspase-3 after polyamine depletion." *J. Biol. Chem.* 279(21):22539-22547.

Dorr, et al., "Modulation of Etoposide Cytotoxicity and DNA Strand Scission in L1210 and 8226 Cells by Polyamines," Cancer Research, Aug. 1996, No. 46, pp. 3891-3895.

Nesbit, et al., "MYC oncogenes and human neoplastic disease," Oncogene, 1999, No. 18, pp. 3004-3016.

Patent Cooperation Treaty, "International Preliminary Report on Patentability and Written Opinion," in corresponding International application No. PCT/US2006/048412, mailed Jun. 24, 2008, 7 pgs.

Patent Cooperation Treaty, "International Search Report," in corresponding International application No. PCT/US2006/048412, mailed May 11, 2007, 4 pgs.

* cited by examiner

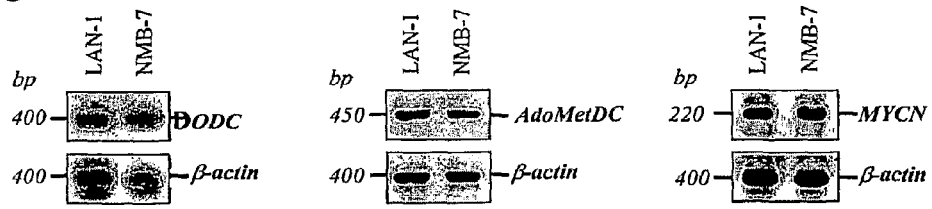
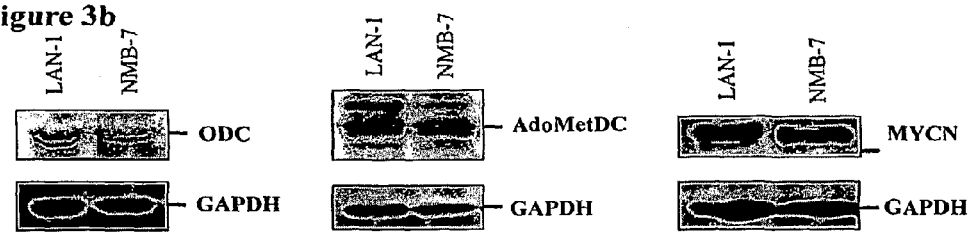
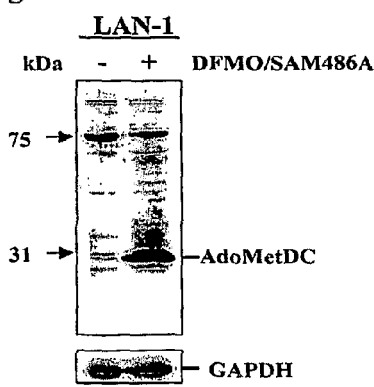
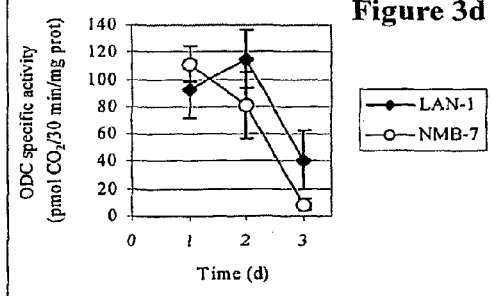
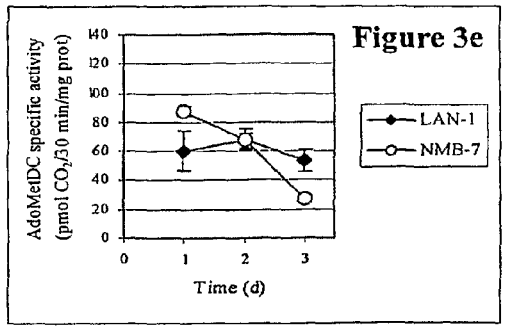

Figure 4a
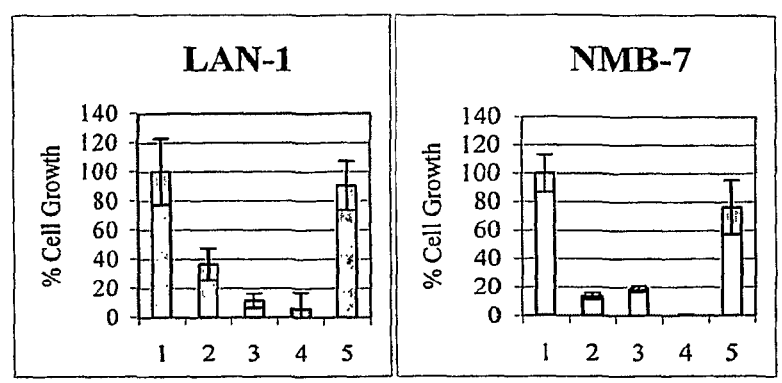
Figure 4b
Control
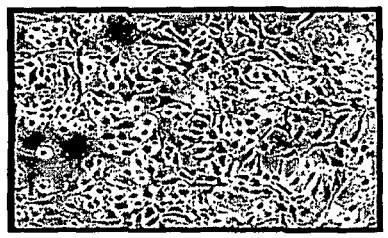 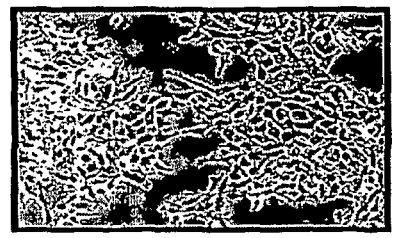
DFMO
 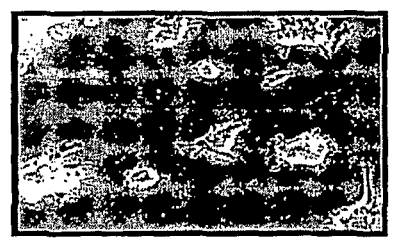
SAM486A
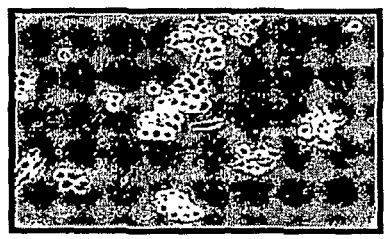 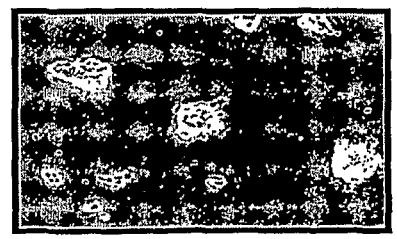
DFMO + SAM486A
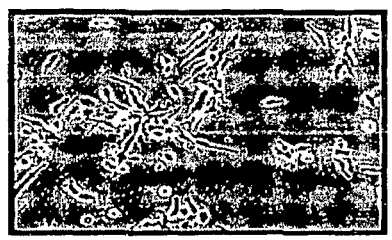 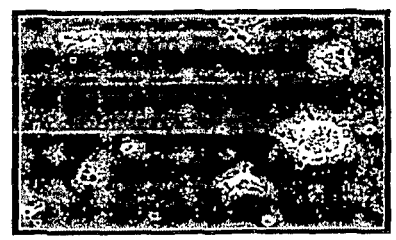
DFMO + SAM486A + Spd
 
LAN-1  NMB-7

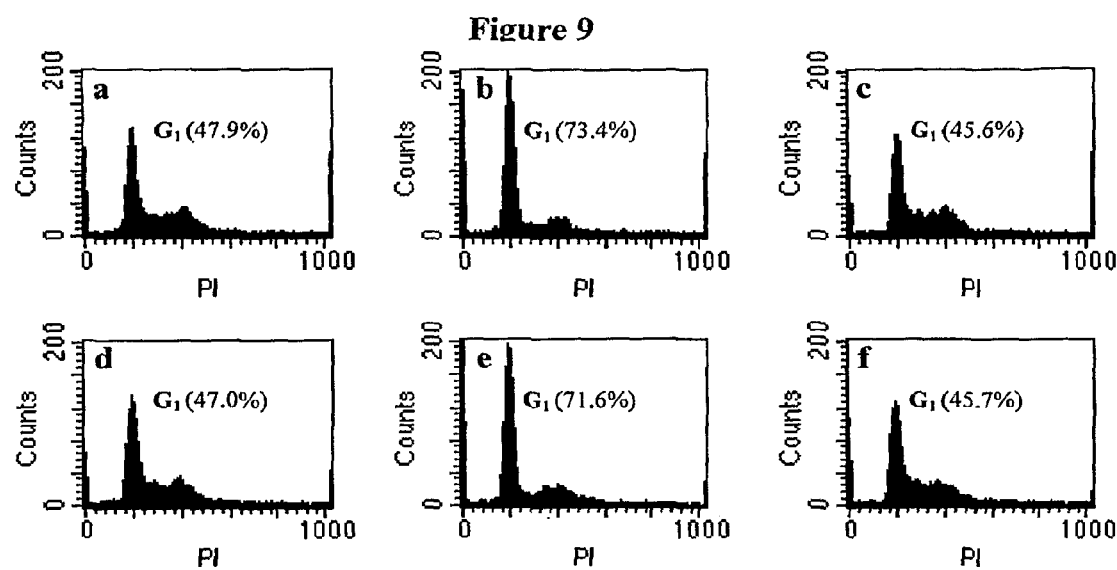

TREATMENT REGIMEN FOR N-MYC, C-MYC, AND L-MYC AMPLIFIED AND OVEREXPRESSED TUMORS

CROSS-REFERENCE TO RELATED APPLICATION

This application claims priority to U.S. Provisional Patent Application Ser. No. 60/752,414 (which is incorporated herein by reference in its entirety), filed on Dec. 20, 2005.

STATEMENT REGARDING FEDERALLY SPONSORED R&D

Certain aspects of this disclosure were supported by NIH grant R01CA111419.

BACKGROUND OF THE INVENTION

1. Field of the Invention

This invention relates to compositions and methods for treating diseases, in particular cancer.

2. Description of the Related Art

Cancer continues to be a major health problem in the United States and the rest of the world. A great deal of money and time is spent each year investigating new therapies and searching for new compounds that have the potential to decrease the mortality associated with cancer. There is also a great deal of effort expended in efforts to decrease the toxicity of existing compounds and therapies.

Neuroblastoma (NB) is the most common extracranial tumor of childhood with approximately 700 new cases per year in the United States. While many infants experience complete regression of primary tumors and even metastatic disease, older children are often confronted with NB metastases that are aggressive and respond poorly to even the most intense multi-component drug regimens. MYCN proto-oncogene amplification occurs in approximately 20% of primary NB tumors, and is strongly associated with advanced stage disease, rapid tumor progression, and poor prognosis (Brodeur G M. (2003) *Nat Rev Cancer,* 3, 203-16; Brodeur et al., (1984) *Science,* 224, 1121-4; Seeger et al., (1985). *N Engl J Med,* 313, 1111-6, each of which is incorporated herein by reference in its entirety).

Polyamine (PA) levels are elevated in many types of cancer, and interference with PA biosynthesis has long been considered a promising therapeutic approach against proliferative diseases, including various malignancies (Schipper et al., (2003) *Biochem Soc Trans* 31, 375-380; Thomas, T., and Thomas, T. J. (2003) *J Cell Mol Med* 7, 113-126; Davidson et al., (1999) *Endocr Relat Cancer* 6, 69-73; Bachrach, U. (2004) *Amino Acids* 26, 307-309. Epub 2004 June 2022; Milovic, V., and Turchanowa, L. (2003) *Biochem Soc Trans* 3.1, 381-383; Seiler, N. (2003) *Curr Drug Targets* 4, 565-585; Seiler, N. (2003) *Curr Drug Targets* 4, 537-564; Nishioka, K. (1996) *Polyamines in cancer: basic mechanisms and clinical approaches*; McCann, P. P., and Pegg, A. E. (1992) *Pharmacol Ther* 54, 195-215; Heby, O., and Persson, L. (1990) *Trends Biochem Sci* 15, 153-158, each of which is incorporated herein by reference in its entirety). Elevated PA levels have also been detected in urine of cancer patients and can be measured in blood and cerebrospinal fluids (Wallace, H. M., Fraser, A. V., and Hughes, A. (2003) *Biochem J* 376, 1-14; Bachrach, U. (2004) *Amino Acids* 26, 307-309. Epub 2004 June 2022; Russell, D. H. (1971) *Nat New Biol* 233, 144-145, each of which is incorporated herein by reference in its entirety). The naturally occurring PAs are small aliphatic cations. PAs are found in all living cells and are responsible for a plethora of functions including cell growth, differentiation, apoptosis, and DNA replication (Cohen, S. S. (1998) *A guide to the polyamines,* Oxford University Press, New York; Pegg, A. E. (1986) *Biochem J* 234, 249-262; Thomas, T., and Thomas, T. J. (2001) *Cell Mol Life Sci* 58, 244-258, each of which is incorporated herein by reference in its entirety).

Mammalian cells produce the PAs putrescine, spermidine, and spermine (Pegg, A. E. (1986) *Biochem J* 234, 249-262; Tabor, C. W., and Tabor, H. (1984) *Annu Rev Biochem* 53, 749-790, each of which is incorporated herein by reference in its entirety). FIG. 1 shows a diagram of the polyamine (PA) biosynthetic pathway and associated amino acids of the urea cycle showing enzymes ODC and AdoMetDC and their specific inhibitors DFMO and SAM486A, respectively. Abbreviations are: AdoMet, S-adenosylmethionine; AdoMetDC, S-adenosylmethionine decarboxylase; AS, argininosuccinate; DFMO, α-difluoromethylornithine (also known as Eflornithine); ODC, ornithine decarboxylase; SAM486A, 4-amidinoindan-1-one 2'-amidinohydrazone (also known as CGP48664A). The diamine putrescine is formed from ornithine via the action of ornithine decarboxylase (ODC), a key enzyme in PA biosynthesis (FIG. 1). Putrescine can be further converted into the higher PAs spermidine and spermine. The aminopropyl groups necessary for these conversions are provided via decarboxylation of S-adenosylmethionine (AdoMet) to decarboxylated S-adenosylmethionine (dcAdoMet) (FIG. 1) (Pegg et al., (1998) *Biochem Soc Trans* 26, 580-586, which is incorporated herein by reference in its entirety). The positively charged PAs allow for both electrostatic and hydrophobic interactions with DNA, RNA, and proteins, thereby directly affecting gene regulation. There is also increasing evidence that PAs are involved at various stages of signal transduction, and, for example, regulate and phosphorylate important cellular components of the MAPK and PI3K signaling pathways (Chen et al., (2003) *Cancer Res* 63, 3619-3625; Bachrach, et. al, (2001) *News Physiol Sci* 16, 106-109; Zhang et. al, (2004) *J Biol Chem* 279, 22539-22547. Epub 22004 March 22515, each of which is incorporated herein by reference in its entirety).

Normal cell growth and proliferation is orchestrated in a cyclic manner by the action of cyclins and cyclin-dependent kinases (cdks) (Pines, J. (1994) *Semin Cancer Biol* 5, 305-313, which is incorporated herein by reference in its entirety) and appropriate activation/inactivation of these proteins is necessary for cell cycle progression. The cyclins A, B, D, and E form complexes with corresponding cdks and specifically regulate the $G_1/S$ and $G_2/M$ phases of the cell cycle. Similarly, ODC and PA concentrations increase in both cell cycle phases (Heby, O. (1981) *Differentiation* 19, 1-20; Wallace, H. M., Fraser, A. V., and Hughes, A. (2003) *Biochem J* 376, 1-14, each of which is incorporated herein by reference in its entirety). This strong positive relationship to cell cycle regulation provides further evidence that PAs are intrinsically linked to cell growth and proliferation (Oredsson, S. M. (2003) *Biochem Soc Trans* 31, 366-370, which is incorporated herein by reference in its entirety).

The proto-oncogene ODC is a key enzyme in polyamine biosynthesis and catalyzes the conversion of ornithine (Orn) to putrescine (Put). The latter is further converted to the higher polyamines spermidine (Spd) and spermine (Spm), all of which have been implicated in tumor cell growth and proliferation. A second rate-limiting enzyme in polyamine biosynthesis is AdoMetDC, which provides the aminopropyl donor decarboxylated S-adenosylmethionine and is required for the sequential conversions of Put to Spd and Spm. Specific inhibitors for both ODC and AdoMetDC are available and have been used in polyamine-related studies.

Alpha-difluoromethylornithine (DFMO, also known as Eflornithine) is a synthetic suicide inhibitor of ODC, which has been evaluated in phase III human clinical trials as an anticancer and chemopreventive agent (Carbone et al., (2001) *Cancer Epidemiol Biomarkers Prev*, 10, 657-61; Fabian et al., (2002) *Clin Cancer Res*, 8, 3105-17; Levin et al., (2003) *Clin Cancer Res*, 9, 981-90; Levin et al., (2000) *Clin Cancer Res*, 6, 3878-84; Meyskens et al., (1999) *Clin Cancer Res*, 5, 945-51; Porter et al., (1992) *Falk symposium on polyamines in the gastrointestinal tract* pp 301-22, each of which is incorporated herein by reference in its entirety). SAM486A (also known as CGP48664), a derivative of the first generation AdoMetDC inhibitor mitoguazone (MGBG), exerts potent and specific inhibition of AdoMetDC (Regenass et al., (1994) *Cancer Res*, 54, 3210-7; Svensson F, Mett H and Persson L. (1997). *Biochem J*, 322, 297-302, each of which is incorporated herein by reference in its entirety). Its efficacy has been assessed in various cancer cells and animal systems (Dorhout et al., (1995) *Int J Cancer*, 62, 738-42; Regenass et al., (1994) *Cancer Res*, 54, 3210-7; Svensson et al., (1997) *Biochem J*, 322, 297-302, each of which is incorporated herein by reference in its entirety), and has been evaluated in Phase I and Phase II human clinical trials (Eskens et al., (2000) *Clin Cancer Res*, 6, 1736-43; Paridaens et al., (2000) *Br J Cancer*, 83, 594-601; Pless et al., (2004) *Clin Cancer Res*, 10, 1299-305; Siu et al., (2002) *Clin Cancer Res*, 8, 2157-66; van Zuylen et al., (2004) *Clin Cancer Res*, 10, 1949-55, each of which is incorporated herein by reference in its entirety). The high enzymatic activities of ODC and AdoMetDC in rapidly growing cells and tissues, and especially, in tumor cells, rendered a rationale for designing pharmacological inhibitors, which selectively interfere with the natural biosynthesis of PAs and, consequently, prevent tumor cell growth and proliferation.

Although monotherapy with DFMO has been disappointing in most cancer trials, the drug was found more effective as a chemopreventive agent based on its low toxicity. The reported side effects are relatively mild with occasional occurrence of temporary ototoxicity, diarrhea, and some neutropenia. Notably, DFMO is successfully used in the treatment of a number of parasitic diseases, including the infection with *Trypanosoma brucei gambiense*, which causes African trypanosomiasis (Heby, et al., (2003) *Biochem Soc Trans* 31, 415-419, which is incorporated herein by reference in its entirety). Recent Phase II clinical trials with SAM486A in patients with relapsed or refractory non-Hodgkin's lymphoma were promising and the most frequent side effects included nausea, vomiting, diarrhea, asthenia, abdominal pain, and flushing (Pless et al., (2004) *Clin Cancer Res* 10, 1299-1305, which is incorporated herein by reference in its entirety).

It has been found that NB cells respond more rapidly and more profoundly to the growth and proliferation inhibitory effects of DFMO and SAM486A than, for example, ovarian cancer cells or other cell lines discussed in the literature (FIG. 2). Our research further revealed that DFMO and SAM486A are effective against NB cells with MYCN amplification (typically derived from more aggressive NB tumors, which metastasize and do not respond well to conventional chemotherapy) and with mutated tumor suppressor protein p53 (often found in relapsed and chemoresistant NB tumors), thus further supporting the use of these drugs for therapeutic NB treatments.

SUMMARY OF THE INVENTION

The use of DFMO and SAM486A in conjunction with other therapeutic compounds has not been previously disclosed. It is believed that the combination of DFMO and SAM486A with other therapeutic compounds will be more effective at treating disease than the combination of DFMO and SAM486A. It is also believed that the combination of DFMO and SAM486A with other therapeutic compounds will be a safer means of treating disease than the combination of DFMO and SAM486A. In particular, it is believed that the combination of DFMO and SAM486A with other therapeutic compounds will be safer and more effective in treating cancer, in particular cancers involving N-MYC, c-MYC, and L-MYC amplified and overexpressed tumors, than the combination of DFMO and SAM486A. It is also believed that the combination of DFMO and SAM486A with other therapeutic compounds will be safer and more effective in treating neuroblastomas than the combination of DFMO and SAM486A. In particular, it is believed that the use of a combination comprising DFMO, SAM486A, and other therapeutic compounds, will allow use of a lower dose of each component of the combination than would be needed if the drugs were administered individually.

Thus, in some embodiments the present invention includes a composition comprising DFMO and SAM486A in conjunction with other compounds.

In other embodiments, the present invention includes a method of treating infectious diseases in a mammal by providing effective amounts of DFMO and SAM486A in combination with effective amounts of other therapeutic compounds.

In some embodiments, the present invention provides a method of inhibiting abnormal cell growth and proliferation in a mammal by providing effective amounts of DFMO, SAM486A in combination with effective amounts of other therapeutic compounds.

In some embodiments, the invention includes a method of treating cancer in a mammal by providing effective amounts of DFMO and SAM486A in combination with effective amounts of other therapeutic compounds. In some embodiments, the present invention includes methods of treating N-MYC, c-MYC, and L-MYC amplified and overexpressed tumors in a mammal by providing effective amounts of DFMO and SAM486A in combination with effective amounts of other therapeutic compounds. In some embodiments, the N-MYC, c-MYC, and L-MYC amplified and overexpressed tumor is a neuroblastoma.

In some embodiments, the invention is a composition comprising: DFMO, SAM486A, a retinoid, and any cytotoxic drug. In some embodiments the cytotoxic drug is bleomycin, busulfan, chlorambucil, cisplatin, cyclophosphamide, cytarabine, decarbazine, daunorubicin, DL-Buthionine (S,R)-sulfoximine, doxorubicin, etoposide, 5-fluorouracil, hydroxyurea, [$^{131}$I]MIBG, irinotecan, mechloroehamine, melphalan, 6-mercaptopurine, methotrexate, mitoxantrone, paclitaxel, pentostatin, procabazine, topotecan (hycamtin), vinblastine, or vincristine. In other embodiments, the cytotoxic drug is paclitaxel, topotecan, or irinotecan. In other embodiments, the retinoid is fenritidine or 13 cis retinoic acid. In some embodiments the cytotoxic drug is a polyamine analog. In some embodiments, the polyamine analog is CGC-11047, CGC-11093, DENSpm, or SL-11144.

In some embodiments, the present invention is a method of inhibiting abnormal cell proliferation in a mammal, that includes administering an effective amount of DFMO, SAM486A, a retinoid, and any cytotoxic drug. In some embodiments, the cytotoxic drug is bleomycin, busulfan, chlorambucil, cisplatin, cyclophosphamide, cytarabine, decarbazine, daunorubicin, DL-Buthionine (S,R)-sulfoximine, doxorubicin, etoposide, 5-fluorouracil, hydroxyurea,

[¹³¹I]MIBG, irinotecan, mechloroehamine, melphalan, 6-mercaptopurine, methotrexate, mitoxantrone, paclitaxel, pentostatin, procabazine, topotecan (hycamtin), vinblastine, or vincristine. In some embodiments, the cytotoxic drug is paclitaxel, topotecan, or irinotecan. In some embodiments, the cytotoxic drug is a polyamine analog. In some embodiments, the method further includes putting the mammal on a low-polyamine diet. In some embodiments, the putting the mammal on a low-polyamine diet includes providing the patient with dietary instructions. In some embodiments, the putting the mammal on a low-polyamine diet includes providing the patient with low polyamine meal replacements. In some embodiments the retinoid is fenritidine or 13 cis retinoic acid.

In some embodiments, the present invention is a method of treating an infectious disease in a mammal, that includes administering an effective amount of DFMO, SAM486A, retinoic acid, and any cytotoxic drug; and placing the mammal on a polyamine-deficient diet.

In some embodiments, the present invention is a method of treating cancer in a human, that includes administering an effective amount of DFMO, SAM486A, retinoic acid, and any cytotoxic drug; and placing the human on a polyamine-deficient diet.

In some embodiments, the present invention is the use of DFMO, SAM486A, a retinoid, and any cytotoxic drug, in making a medicament suitable for treating cancer. In some embodiments, the cytotoxic drug is bleomycin, busulfan, chlorambucil, cisplatin, cyclophosphamide, cytarabine, decarbazine, daunorubicin, DL-Buthionine (S,R)-sulfoximine, doxorubicin, etoposide, 5-fluorouracil, hydroxyurea, [¹³¹I]MIBG, irinotecan, mechloroehamine, melphalan, 6-mercaptopurine, methotrexate, mitoxantrone, paclitaxel, pentostatin, procabazine, topotecan (hycamtin), vinblastine, and vincristine. In some embodiments the cytotoxic drug is paclitaxel, topotecan, or irinotecan. In some embodiments, the retinoid is fenritidine or 13 cis retinoic acid. In some embodiments, the cytotoxic drug is a polyamine analog. In some embodiments the polyamine analog is CGC-11047, CGC-11093, DENSpm, or SL-11144.

In some embodiments, the present invention is a kit that includes DFMO; SAM486A; retinoic acid; a cytotoxic drug; and instructions identifying foods that are polyamine free.

In some embodiments, the present invention is a kit that includes DFMO; SAM486A; retinoic acid; a cytotoxic drug; and low polyamine meal replacements.

In some embodiments, the present invention is a composition comprising a polyamine analog, a cytotoxic drug, and a retinoid. In some embodiments, the cytotoxic drug is bleomycin, busulfan, chlorambucil, cisplatin, cyclophosphamide, cytarabine, decarbazine, daunorubicin, DL-Buthionine (S,R)-sulfoximine, doxorubicin, etoposide, 5-fluorouracil, hydroxyurea, [¹³¹I]MIBG, irinotecan, mechloroehamine, melphalan, 6-mercaptopurine, methotrexate, mitoxantrone, paclitaxel, pentostatin, procabazine, topotecan (hycamtin), vinblastine, or vincristine. In some embodiments, the cytotoxic drug is paclitaxel, topotecan, or irinotecan. In some embodiments the retinoid is fenritidine or 13 cis retinoic acid. In some embodiments the polyamine analog is CGC-11047, CGC-11093, DENSpm, or SL-1144.

BRIEF DESCRIPTION OF THE DRAWINGS

FIG. 3 shows expression and activity studies of ODC, AdoMetDC, and MYCN in NB cells.

FIG. 4 shows effects of polyamine inhibitors DFMO and SAM486A on the growth and proliferation of human NB cells.

FIG. 9 contains histograms showing cell cycle phase distributions of various samples being treated by different compounds (see Table 3).

DETAILED DESCRIPTION OF THE PREFERRED EMBODIMENTS

Figure 6:
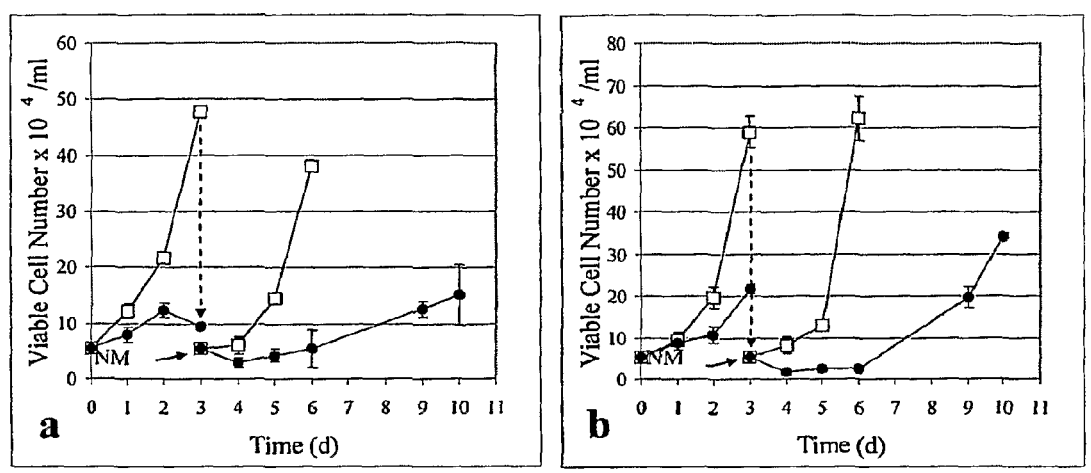
FIG. 6 shows prolonged cell growth and proliferation inhibition of inhibitor-treated human NB cells. Proliferation of cell lines (a) LAN-1 and (b) NMB-7 in the absence (□) or the presence (●) of 5 mM DFMO plus 10 µM SAM486A.

Polyamine inhibitors DFMO and SAM486A interfere with ODC and AdoMetDC enzyme activities, cause polyamine depletion, and ultimately, disturb cell cycle progression at the $G_1/S$ transition, which leads to growth/proliferation arrest. The combination of both inhibitors generally intensifies these effects (Table 3, FIG. 4a, and FIG. 7). Growth inhibition of cells treated with a combination of DFMO and SAM486A was sustained even after removal of inhibitors, thus suggesting prolonged growth and proliferation arrest (FIG. 6). Based largely upon the method of action of DFMO and SAM486A, the use of this combination with certain other therapeutic compounds should be even more effective in treating infectious diseases and cancers (in particular neuroblastomas). In particular, DFMO and SAM486A combined with a cytotoxic drug, and retinoic acid should be even more effective than DFMO and SAM486A in treating infectious diseases and cancers, in particular neuroblastomas.

In addition, it is expected that many other tumor types are responsive to the combination of drug compounds. For example, the compounds and methods of the present invention should be effective treatments for N-MYC, c-MYC, and L-MYC amplified and overexpressed tumors. Examples of N-MYC amplified tumors include neuroblastoma, small cell lung cancer, alveolar rhabdomyosarcoma, and retinoblastoma. Examples of c-MYC and L-MYC amplified or overexpressed tumors include bladder cancer, breast cancer, colon cancer, gastric cancer, hepatoca, melanoma, myeloma, ovarian cancer, prostate cancer, and small cell lung cancer.

Moreover, other pathological conditions (e.g., fungal, bacterial, parasitic, viral infections) may be treatable with the compounds and methods of the present invention. For example, DFMO alone is used by the World Health Organization to treat African sleeping sickness (trypanosomiasis). Thus, it is contemplated that an improved DFMO cocktail is likely to further improve the therapeutic effectiveness and reduce the dose of DFMO required to achieve the therapeutic effect.

Further it is contemplated that the drug cocktail and associated kits and methods of the present invention will reduce the toxicity of the individual components of the combination because a lower dose of each compound will be required to achieve the desired therapeutic effect. In particular, the combination and related methods of the present invention will permit use of DFMO in a lower dose. Currently DFMO is administered at very high doses (estimated at 1 kilogram per patient, per clinical trial). Although severe side-effects are not observed with DFMO, lowering the dose will lower the side-effects that are present and reduce therapy cost. Alternatively, DFMO may be kept at higher doses allowing the reduction of cytotoxic drug concentration thereby lowering otherwise significant side effects as typically known (e.g. hair loss, other organ failure, sterility).

Mechanism of DFMO and SAM486A Activity

The proteins $p27^{Kip1}$, Rb, and MYCN play a key role in polyamine inhibitor-induced $G_1$ cell cycle arrest in MYCN-amplified NB cells. Unlike DFMO and DFMO/SAM486A, it was found that SAM486A alone had almost no effect on $p27^{Kip1}$, Rb, and MYCN despite its profound effects on polyamine pools, $G_1$ arrest, and NB cell growth and proliferation and morphology. Although the reason for this is unclear, the inventors, without wishing being tied to any particular theory of activity, suspect that other cell signaling molecules are involved in the observed SAM486A-induced growth and proliferation arrest, which are yet to be identified.

Figure 1:
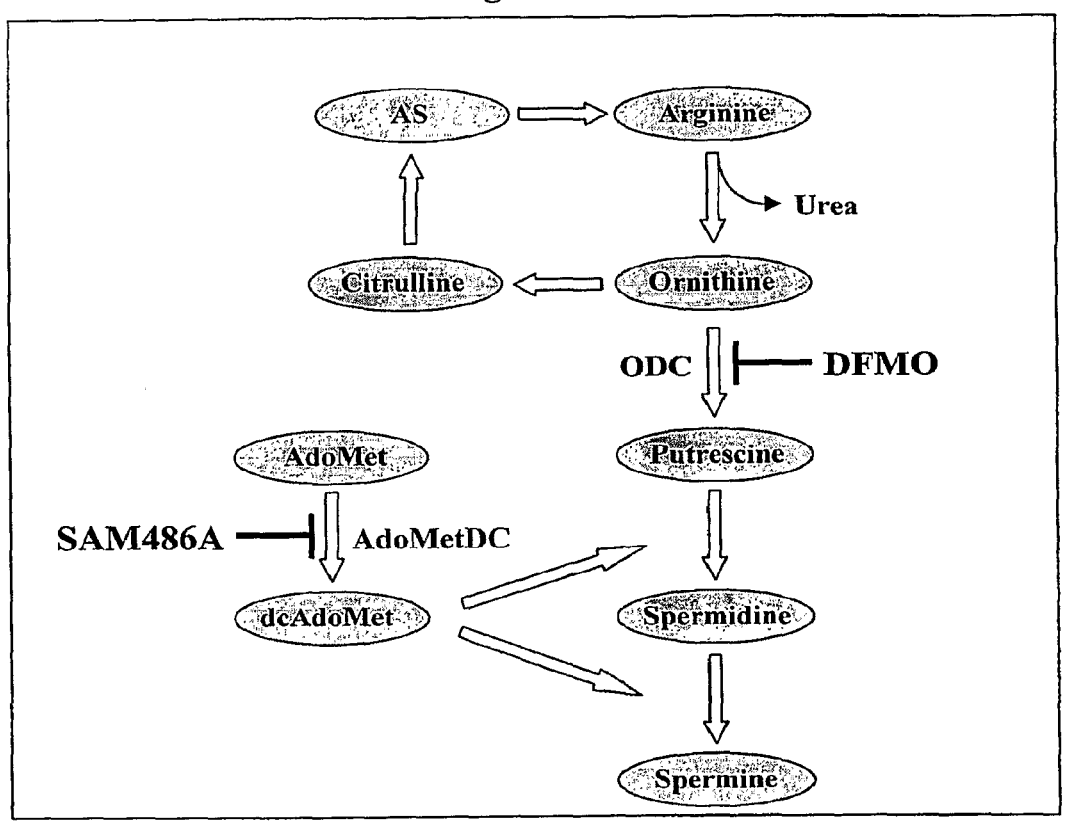
FIG. 1 is a simplified diagram of the polyamine (PA) biosynthetic pathway and associated amino acids of the urea cycle.

(1988) Cancer Res 48, 759-774, hereby incorporated by reference in its entirety), and therefore, the enzyme AdoMetDC represents a second rational target (FIG. 1). Since the two enzymes are co-regulated by intracellular PA pools so that inhibition of one results in a compensatory increase in the other, it follows that targeted interference with a drug cocktail composed of ODC inhibitor DFMO and AdoMetDC inhibitor SAM486A (or other prospective PA inhibitors of clinical relevance) is likely to sharpen the antiproliferative effects by complete depletion of the PA pools.

Figure 7A:
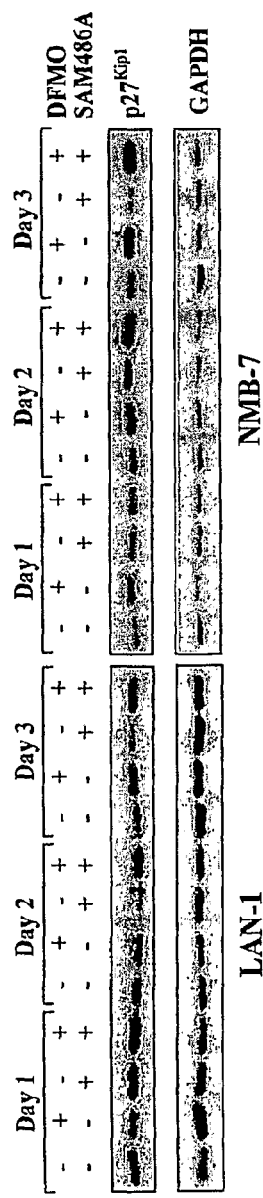
FIG. 7 shows a Western blot analyses of inhibitor-treated human NB cells. Effect on (a) cyclin-dependent kinase inhibitor p27$^{Kip1}$, (b) retinoblastoma protein Rb (phosphorylations at Ser795 and Ser807/811, and detection of total Rb) and (c) MYCN in LAN-1 and NMB-7 cells treated with 5 mM DFMO, 10 µM SAM486A or the combination of both inhibitors.
Figure 7B:
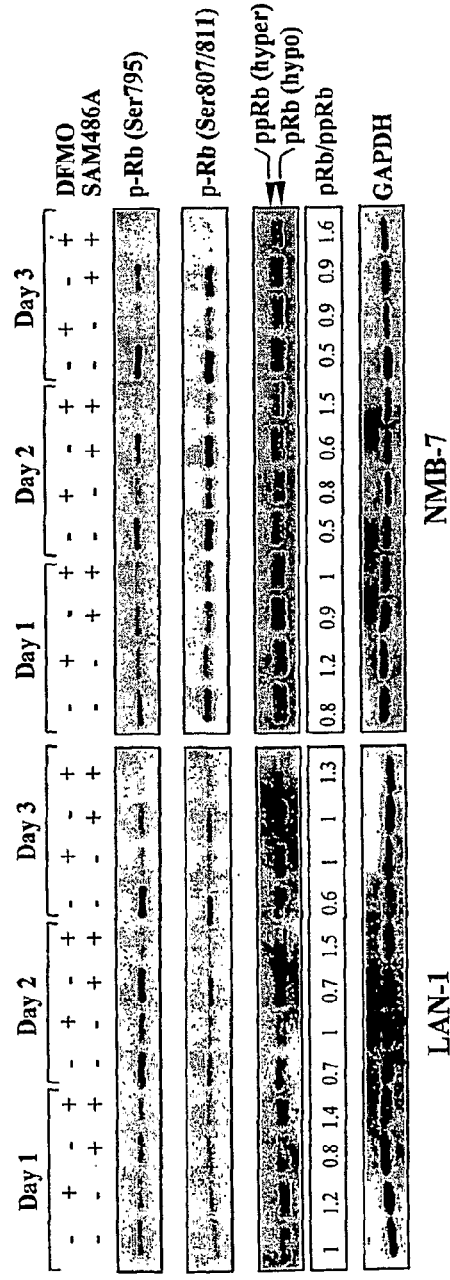

It has been found that the protein levels of $p27^{Kip1}$ sharply increased in the presence of DFMO alone or combined with SAM486A (FIG. 7a). This increase in $p27^{Kip1}$ is tightly correlated with hypophosphorylation of Rb (FIG. 7b). Since Rb is a known regulator of $G_1$/S transition, it is conceivable that the polyamine inhibitor-induced $G_1$ cell cycle arrest in LAN-1 and NMB-7 cells is regulated by Rb hypophosphorylation in response to $p27^{Kip1}$. Similarly, it was shown that $p27^{Kip1}$ is a key mediator of RA-induced growth and proliferation arrest in NB cells (Matsuo & Thiele, (1998) Oncogene, 16, 3337-43, which is incorporated herein by reference in its entirety). Such findings are also in partial agreement with results obtained with other cell systems, such as normal rat intestinal epithelial cells IEC-6 (Ray et al., (1999) Am J Physiol, 276, C684-91, which is incorporated herein by reference in its entirety), human breast cancer cells MDA-MB-468 (Singh et al., (2001) Carcinogenesis, 22, 1863-9, which is incorporated herein by reference in its entirety), and human melanoma cells MALME-3 (Kramer et al., (2001) Cancer Res, 61, 7754-62). However, in those cell lines, polyamine

TABLE 1

Effects of polyamine inhibitors on polyamine pools in human neuroblastoma cells

| | | POLYAMINE POOLS (NMOL/MG TOTAL PROTEIN)[B] | | | | | | | | |
|---|---|---|---|---|---|---|---|---|---|---|
| | | Day 0 | | | Day 2 | | | Day 3 | | |
| CELL LINE | TREATMENT[A] | PUT | SPD | SPM | PUT | SPD | SPM | PUT | SPD | SPM |
| LAN-1 | Control | 1.2 | 11.9 | 15.3 | 0.6 | 9.4 | 11.8 | 0.1 | 7.1 | 9.4 |
| | DFMO | | | | 0.3 | 2.2 | 8.7 | 0.0 | 1.9 | 8.1 |
| | SAM486A | | | | 48.5 | 5.5 | 4.2 | 43.7 | 5.0 | 3.5 |
| | DFMO/SAM486A | | | | 0.3 | 2.6 | 9.0 | 0.1 | 1.4 | 6.9 |
| | DFMO/SAM486A/Spd | | | | 0.0 | 21.1 | 4.2 | 0.4 | 16.9 | 3.5 |
| NMB-7 | Control | 5.6 | 13.9 | 11.2 | 2.6 | 12.7 | 11.2 | 0.8 | 8.4 | 12.6 |
| | DFMO | | | | 0.1 | 1.9 | 9.3 | 0.0 | 1.4 | 8.6 |
| | SAM486A | | | | 69.6 | 5.6 | 3.9 | 259.5 | 5.5 | 3.6 |
| | DFMO/SAM486A | | | | 0.7 | 5.1 | 7.4 | 0.6 | 1.9 | 9.8 |
| | DFMO/SAM486A/Spd | | | | 0.1 | 22.6 | 6.9 | 0.1 | 40.6 | 3.4 |

[A]DFMO = 5 mM; SAM486A = 10 μM; Spd = 10 μM.
[B]Data represent the mean values of two independent experiments.

The data suggest the combined administration of DFMO and SAM486A provides an effective means for the treatment of NB tumors and N-MYC, C-MYC, and L-MYC amplified and overexpressed tumors. DFMO and SAM486A cause rapid and prolonged growth and proliferation inhibition of two MYCN-amplified NB cell lines, which 1) are representative of MYCN-amplified tumors with aggressive behavior, and 2) are deficient in p53. Mutated p53 is often associated with relapsed and more progressive tumors, which circumvent p53-mediated apoptosis and exhibit chemoresistance (Hopkins-Donaldson et al., (2002) Oncogene, 21, 6132-7, which is incorporated herein by reference in its entirety).

Although ODC has generally been considered as the enzyme catalyzing the rate-limiting step in PA biosynthesis, it has been shown that the supply of dcAdoMet represents a second rate-limiting factor in PA biosynthesis (Pegg, A. E.

inhibitor-induced $G_1$ arrest was primarily regulated by $p21^{Waf1/Cip1}$ and p53, while DFMO and DFMO/SAM486A in LAN-1 and NMB-7 cells increased $p27^{Kip1}$, in the absence of both $p21^{Waf1/Cip1}$ and p53. Furthermore, in contrast to the rapid growth and proliferation inhibition observed in NB cells (FIG. 4), IEC-6 and MALME-3 cells required treatments of up to 10 days with DFMO (Ray et al., (1999) Am J Physiol, 276, C684-91, which is incorporated herein by reference in its entirety) or 8-12 days with DFMO plus MDL-73811 (another AdoMetDC inhibitor) (Kramer et al., (2001) Cancer Res, 61, 7754-62, which is incorporated herein by reference in its entirety), respectively, and showed almost no alterations in cell morphology. This suggests that DFMO and SAM486A are more potent in NB cells, and possibly, also more successful in killing NB tumors.

Figure 7C:
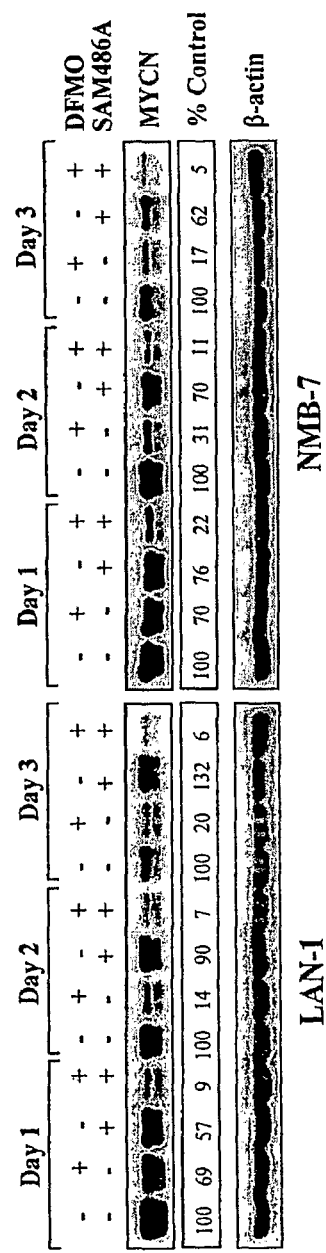
Figure 8:
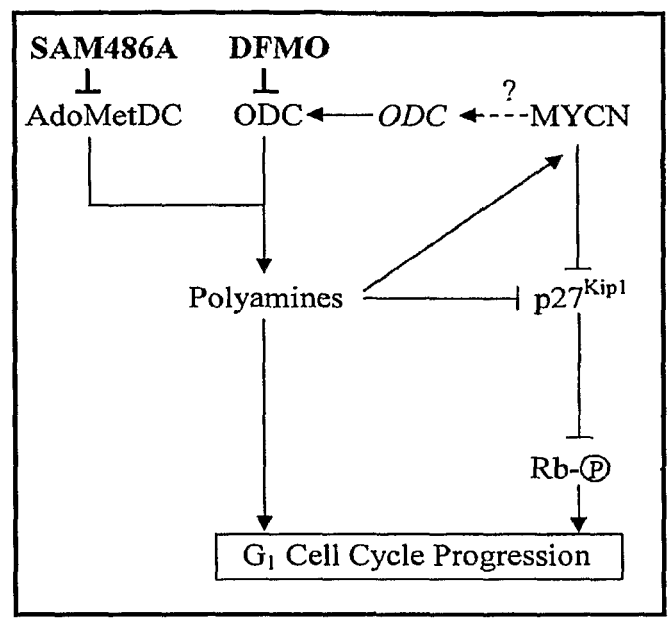
FIG. 8 shows the proposed interplay between polyamines and cell cycle regulatory proteins in MYCN-amplified NB cells.

Down regulation of MYCN has been of great interest with regard to developing advanced NB therapies and should prove effective in treating all N-MYC amplified tumors and also C-MYC and L-MYC amplified and overexpressed tumors. It has previously been shown that DFMO blocks the expression of c-Myc (Tabib & Bachrach, (1994) *Biochem Biophys Res Commun*, 202, 720-7, which is incorporated herein by reference in its entirety) and these findings are extended by our own results, which show strong downregulation of the c-Myc-related protein MYCN in response to DFMO or DFMO/SAM486A (FIG. 7c). It has also been shown that MYCN can regulate p27$^{Kip1}$ in NB cells by targeting p27$^{Kip1}$ to the proteasome (Nakamura et al., (2003) *Cell Death Differ*, 10, 230-9, which is incorporated herein by reference in its entirety), and it is therefore possible that the observed increase in p27$^{Kip1}$ is in response to a decrease in MYCN. FIG. 6 shows the possible involvement of polyamines in the regulation of p27$^{Kip1}$, Rb, and MYCN in LAN-1 and NMB-7 cells based on our observations. The regulation of ODC by MYCN has been previously proposed (Ben-Yosef et al., (1998) *Oncogene*, 17, 165-71; Lu et al., (2003) *Cancer Lett*, 197, 125-30; Lutz et al., (1996) *Oncogene*, 13, 803-12, each of which is incorporated herein by reference in its entirety), but has not been definitively confirmed. The precise mechanism by which polyamines regulate MYCN in NB cells remains to be further clarified.

DFMA and SAM486A

Figure 2:
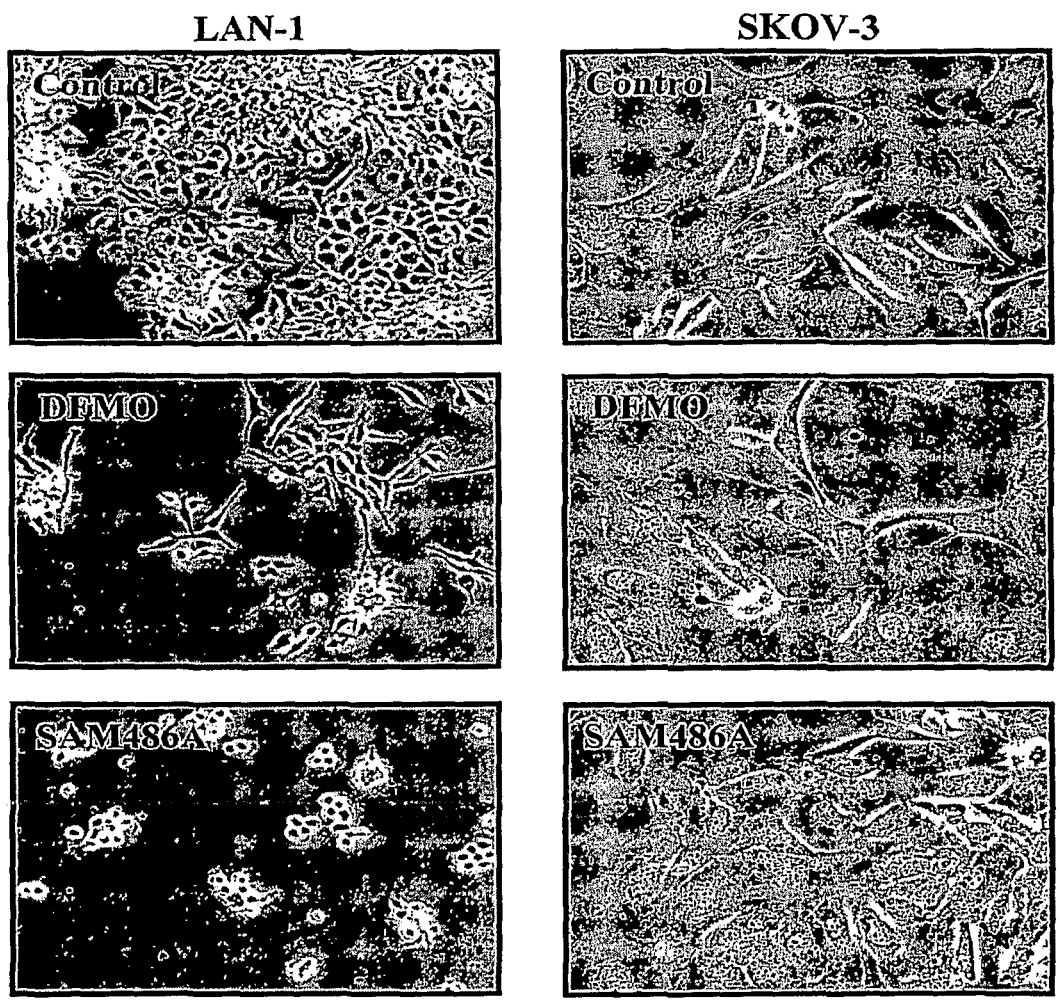
FIG. 2 show the effect of 5 mM DFMO or 10 µM SAM486A on the growth and proliferation of MYCN-amplified and p53 mutant human neuroblastoma (NB) cell line LAN-1 and human ovarian cancer cell line SKOV-3.

DFMO and SAM486A have both been evaluated in human cancer trials, but only individually. FIG. 2 shows an in vitro experiment that explores their individual effectiveness. (Bachmann, A S, (2004) Hawaii Med. Journal, 63:371-373, which is incorporated herein by reference in its entirety). Cells were treated without or with indicated polyamine (PA) inhibitors DFMO or SAM486A for 3 days. Micrographs were taken using an inverted phase contrast microscope (Nikon). In comparison with the ovarian cancer cells SKOV-3, the growth and proliferation of NB cells LAN-1 was inhibited much more drastically and caused significant morphological changes after only 3 days of treatment. This suggests that NB cells are more responsive to PA inhibitors and that the clinically evaluated drugs DFMO and SAM486A will provide an alternative approach for the treatment of NB patients.

In addition, since DFMO and SAM486A have been recently evaluated in Phase III and Phase II human trials, respectively (Levin et al., (2000) *Clin Cancer Res*, 6, 3878-84; Pless et al., (2004) *Clin Cancer Res*, 10, 1299-305, each of which is hereby incorporated by reference in its entirety), there is considerable information available regarding their concurrent side effects, pharmacokinetics, and maximum tolerated doses.

Cytotoxic Compounds

Cytotoxic compounds within the scope of this invention include any compound effective in killing eukaryotic cells, in particular by preventing their reproduction and growth and proliferation. Preferred cytotoxic compounds of the present invention include compounds capable of inhibiting cell growth, cell proliferation, and cell reproduction when administered to a mammal. More preferred cytotoxic compounds include those known in the art to be effective in treating neoplastic cells in humans. Even more preferred cytotoxic compounds of the present invention include bleomycin, busulfan, chlorambucil, cisplatin, cyclophosphamide, cytarabine, decarbazine, daunorubicin, DL-Buthionine (S,R)-sulfoximine, doxorubicin, etoposide, 5-fluorouracil, hydroxyurea, [$^{131}$I]MIBG, irinotecan, mechloroehamine, melphalan, 6-mercaptopurine, methotrexate, mitoxantrone, paclitaxel, pentostatin, procabazine, topotecan (hycamtin), vinblastine, and vincristine. The most preferred cytotoxic compounds are topotecan, irinotecan, and paclitaxel.

Additional useful compounds include polyamine analogs—which can also be considered cytotoxic compounds. Polyamine analogs are thought to down-regulate ornithine decarboxylase (though they do not directly inhibit that enzyme), induce spermidine/spermine $N^1$-acetyltransferase, deplete natural PA pools, inhibit cell growth and proliferation, and induce programmed cell death. Many polyamine analogs are known in the art and known to have cytotoxic effects on different tumor models (by way of nonlimiting example, breast cancer, melanoma, and lung cancer). Examples of polyamine analogs include alkylated analogs, such as $N^1,N^{11}$-Diethylnorspermine (DENSpm), $N^1,N^{11}$-Biethylnorspermine (BENSpm), disethylspermine (DESpm), bisethylspermine (BESpm), disethylhomospermine (DEHSpm), bisethylhomospermine (BEHSpm), BE-4444, BIPSpm, and 3,12-dihydroxy-BEHSpm. Other examples include oligoamines, such as SL11144 (Huang et al., (2003) Clin. Cancer Research 9:2769-77, which is hereby incorporated by reference in its entirety). Additional examples include tetraamine A, tetraamine B, tetraamine CCGC-11047 (www.cellgate.com), CGC-11093 (www.cellgate.com). Additional examples of oligoamines and additional information regarding polyamines can be found in Bacchi et al., (2003) Antimicrob. Agents Chemother., 46:55-61; Woster, M. P., *Polyamine Structure and Synthetic Analogs* at pp. 7-21, found in (2006) *Polyamine Cell Signaling: Physiology, Pharmacology, and Cancer Research* (Wang and Casero Eds.); Hahm, et. al, (2001) Clin. Cancer Research, 7:391-99, each of which is hereby incorporated by reference in its entirety). More preferred polyamine analogs include DENSpm, CGC-11047, CGC-11093, and SL-11144.

Other compounds, such as COX inhibitors, PI3-kinase inhibitors (e.g. LY294002), proteasome inhibitors, histone deacetylase inhibitors (e.g., trichostatin-A), alpha-interferon, DNA vaccines, RNA interference (RNA$_i$) based drugs, and other NB-specific antibody therapies.

Additional compounds include polyamine uptake inhibitors or polyamine export enhancer compounds. These compounds are thought to block extracellular uptake of polyamines into the cell or increase the export of intracellular polyamines out of the cell, respectively.

Retinoic Acid

The Retinoids are a class of chemical compounds that are related chemically to vitamin A (retinol). Examples of retinoids include, fenretinide, retinol, retinal, retinoic acid (including trans-retinoic acid, 13-cis retinoic acid), and their various derivatives. Retinoids have been used in medicine for various purposes, primarily due to the way they regulate epithelial cell growth and proliferation. The use of retinoids in treating neuroblastoma was discussed in Reynolds et al., "Retinoid therapy of high-risk neuroblastoma", Cancer Letters 197 (2003) 185-192, which is hereby expressly incorporated by reference in its entirety. The most preferred retinol for use in the present invention is retinoic acid (RA).

RA is a well-characterized agent that induces neuronal cell differentiation and is used in NB therapy (Tuthill & Wada, (2003) *Hawaii Med J* 62, 224-225, which is incorporated herein by reference in its entirety). In addition, RA affects PA levels and inhibits ODC activity (Cohen, S. S. (1998) *A guide to the polyamines*; Nishioka, K. (1996) *Polyamines in cancer: basic mechanisms and clinical approaches*; Dawson, et al., (1987) *Cancer Res* 47, 6210-6215; Dawson et al., (2001) *Int J Cancer* 91, 8-21, each of which is incorporated herein by reference in its entirety), thus further contributing to the total depletion of PA pools. Downregulation of MYCN expression either by antisense treatment or by RA has been shown to inhibit cell growth and proliferation and/or induce neuronal differentiation of NB cells (Galderisi et al., (1999) *J. Cell Biochem,* 73, 97-105; Galderisi et al., (2003) *Oncogene,* 22, 5208-19; Lu et al., (2003) *Cancer Lett,* 197, 125-30; Matsuo & Thiele, (1998) *Oncogene,* 16, 3337-43, each of which is incorporated herein by reference in its entirety).

Low Polyamine Diets and Polyamine-Limiting Dietary Supplements

Polyamines (Pas) are intrinsically connected to cell growth and proliferation and proliferation, and the inhibition of the sentinel PA biosynthetic enzymes ODC and AdoMetDC is considered a means to prevent cell proliferation by PA depletion, the blockade of cell cycle progression, and interference with signal transduction.

Polyamines play a key role in cell cycle regulation (Wallace et al., (2003) *Biochem J,* 376, 1-14, which is incorporated herein by reference in its entirety), but proteins, which are directly regulated by polyamines are still poorly defined. High polyamine titers promote cell cycle progression and cell proliferation, presumably via the blocking of cyclin-dependent kinase inhibitor $p27^{Kip1}$, which leads to hyperphosphorylation of retinoblastoma protein Rb. The blockade of polyamine biosynthesis with specific inhibitors DFMO and SAM486A leads to $G_1$ cell cycle arrest in response to $p27^{Kip1}$ upregulation and subsequent hypophosphorylation of Rb. MYCN is strongly downregulated in response to polyamine depletion and is known to regulate $p27^{Kip1}$ and ODC gene expression in NB cells. (Wallick et. al, Oncogene, (2005) 24(36):5606-18, which is hereby incorporated by reference in its entirety).

In certain embodiments this invention comprises a treatment regimen that includes placing the patient on a low polyamine diet or providing a polyamine limiting dietary supplement. Some foods and beverages have a relatively high content of polyamines (e.g., orange juice), whereas other foods and beverages contain a relatively low amount of polyamines (e.g., red wine). A low polyamine diet is one that has a polyamine content that is lower than that present in a standard diet. Preferably, a low polyamine diet is one that does not contain any foods or beverages that have a relatively high content of polyamines. More preferably, a low polyamine diet will contain only foods that have a relatively low content of polyamines. Most preferably, a low polyamine diet is one that is essentially free of polyamines. Similarly, a polyamine limiting dietary supplement is preferably a meal replacement drink or shake that contains a low amount of polyamines. Most preferably, a polyamine limiting dietary supplement is a meal replacement drink or shake that is essentially free of polyamines. Most preferably, a patient would ingest this supplement in lieu of at least two regular meals.

Combinations

The present invention encompasses compositions and methods comprising administering DFMO and SAM486A in combination with various other therapeutic compounds. Various combinations are contemplated and encompassed by embodiments of this invention. Preferred combinations include DFMO, SAM486A, and a cytotoxic compound. More preferred combinations include DFMO, SAM486A, a cytotoxic compound, and a retinoid. Even more preferred combinations include DFMO, SAM486A, a cytotoxic compound, retinoic acid, and putting the patient on a low polyamine diet and/or providing the patient a polyamine-limiting dietary supplement.

In addition, other combinations not including DFMO and SAM486A are contemplated. For example, contemplated combinations include the use of one or more polyamine analogs in lieu of DFMO and SAM486A. Preferred combinations include a polyamine inhibitor and another cytotoxic compound. More preferred combinations a polyamine inhibitor and another cytotoxic compound, and a retinoid. Even more preferred combinations include a polyamine inhibitor and another cytotoxic compound, retinoic acid, and putting the patient on a low polyamine diet and/or providing the patient a polyamine-limiting dietary supplement.

The most preferred combinations include: DFMO, SAM486A, topotecan, retinoic acid, and putting the patient on a low polyamine diet and/or providing the patient a polyamine-limiting dietary supplement; DFMO, SAM486A, irinotecan, retinoic acid, and putting the patient on a low polyamine diet and/or providing the patient a polyamine-limiting dietary supplement; DFMO, SAM486A, paclitaxel, retinoic acid, and putting the patient on a low polyamine diet and/or providing the patient a polyamine-limiting dietary supplement; DFMO, SAM486A, topotecan, fenretinide, and putting the patient on a polyamine-free diet and/or providing the patient a polyamine-limiting dietary supplement; DFMO, SAM486A, irinotecan, fenretinide, and putting the patient on a polyamine-free diet and/or providing the patient a polyamine-limiting dietary supplement; DFMO, SAM486A, paclitaxel, fenretinide, and putting the patient on a polyamine-free diet and/or providing the patient a polyamine-limiting dietary supplement.

Kits

The present invention also includes kits. In certain embodiments, the kits may be groupings of the various therapeutic agents described herein. In other embodiments, the kits may also include dietary instructions that provide information to the patient on how to consume a low polyamine diet. In some embodiments, the kits include a polyamine limiting dietary supplement or information regarding polyamine limiting dietary supplements.

Pharmaceutical Compositions

Pharmaceutical compositions of the compounds of the present invention can be prepared in combination with an acceptable pharmaceutical carrier. Suitable carriers can contain inert ingredients that do not interact with the compound. Techniques for the preparation of pharmaceutical compositions are well known in the art and for example described in Remington's Pharmaceutical Sciences (Mack Publishing Company, Easton, Pa.). Suitable pharmaceutical carriers for intravenous and other parenteral administration include, for example, sterile water, physiological saline, bacteriostatic saline (i.e., saline containing about 0.9% mg/ml benzyl alcohol), phosphate-buffered saline, Hank's solution, or Ringer's lactate. Methods for encapsulating compositions (such as in a coating of hard gelatin or cyclodextran) are known in the art (Baker, et al., "Controlled Release of Biological Active Agents", John Wiley and Sons, 1986, which is incorporated herein by reference in its entirety). Suitable carriers for topical administration include commercially available inert gels, liquids supplemented with albumin, methylcellulose, or a collagen matrix. Typical of such formulation are ointments, creams, and gels. Preferred carriers for topical administration are those that facilitate penetration of the skin by the new compound.

Some compounds within the scope of the present invention can be administered orally (e.g., in the form of a pill, tablet, syrup, suspension, or capsule). The compound can also be administered intravenously (e.g., by injection) into the systemic vascular compartment. Still other appropriate modes of administration include systemic administration, intramuscular, intradermal, subcutaneous, and intraperitoneal administration. Some compounds within the scope of the present invention can be applied topically at the site of the disease for example to the skin in case of melanoma. Yet other modes of treatment include administering the compound to the site of cancer during or after surgical removal of cancer for example in case Glioma or other forms of tumors.

The term "pharmaceutically acceptable salt" refers to a formulation of a compound that does not cause significant irritation to an organism to which it is administered and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt (e.g., a sodium or a potassium salt), an alkaline earth metal salt (e.g., a calcium or a magnesium salt), a salt of organic bases such as dicyclohexylamine, N-methyl-D-glucamine, tris(hydroxymethyl) methylamine, and salts thereof with amino acids (e.g., arginine and lysine).

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate. An example, without limitation, of a prodrug would be a compound of the present invention which is administered as an ester (the "prodrug") to facilitate transmittal across a cell membrane where water solubility is detrimental to mobility, but which then is metabolically hydrolyzed to the carboxylic acid, the active entity, once inside the cell where water-solubility is beneficial.

The term "pharmaceutical composition" refers to a mixture of a compound of the invention with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the compound in a local rather than systemic manner, for example, via injection of the compound directly in the renal or cardiac area, often in a depot or sustained release formulation. Thus, delivery to the tumor site or the site of resection surgery is contemplated as one method of the present invention. Furthermore, one may administer the drug in a targeted drug delivery system, for example, in a liposome coated with a tissue-specific antibody. The liposomes will be targeted to and taken up selectively by the organ.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above. The use of prodrugs and pharmaceutically-acceptable salts, including acid addition salts, is also within the scope of the present invention.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Unit dosage forms (pills, tablets, capsules, or other single-dose-containing solid, gel, or liquid forms) are particularly contemplated. Pharmaceutical preparations for oral use can be obtained by mixing one or more solid excipients with pharmaceutical compounds of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Dry powder delivery is also contemplated, which can be used for systemic or localized administration (e.g., treatment of tracheal or lung cancer). Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form (including lyophilized forms and forms that include excipients) for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An exemplary pharmaceutical carrier for compounds of the invention that are hydrophobic or lipophilic is a co-solvent system comprising benzyl alcohol, a nonpolar surfactant, a water-miscible organic polymer, and an aqueous phase. A common co-solvent system used is the VPD co-solvent system, which is a solution of 3% w/v benzyl alcohol, 8% w/v of the nonpolar surfactant POLYSORBATE 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semi-permeable matrices of solid hydrophobic polymers containing the therapeutic agent, or biodegradable or bioerodible materials, such as polylactic acid, polyglycolic acid, copolymers of these or other materials, collagen polymers or matrices, and the like. Various other sustained-release materials have been established and are well known by those skilled in the art. Sustained-release dosage forms may, depending on their chemical nature, release the compounds for a few weeks up to over 100 days. Depending on the chemical nature and the biological stability of the therapeutic reagent, additional strategies for protein stabilization may be employed.

Many of the compounds used in the pharmaceutical combinations of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acid or base forms.

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", Ch. 1 p. 1). Typically, the dose range of the composition administered to the patient can be from about 0.5 to 1000 mg/kg of the patient's body weight.

The dosage may be a single one or a series of two or more given in the course of one or more days, as is needed by the patient. Note that for particular compounds disclosed herein, suitable human dosage can be inferred from $ED_{50}$ or $ID_{50}$ values, or other appropriate values derived from in vitro or in vivo studies, as qualified by toxicity studies and efficacy studies in animals.

For some of the particular compounds used in some embodiments of the invention, preferred dosages are as follows: DFMO 1-5 g/m$^2$, 13 cis retinoic acid 10-30 mg/m$^2$, topotecan 10-180 mg/m$^2$, SAM486A 50-150 mg/m$^2$. DENSpm can be administered from a solution of 30 mg/ml (water) and further diluted into saline. The drug can then be administered on cycles—once a day for 5 consecutive days every 21 days. CGC-11047 can be administered intravenously in cycles—once weekly for three weeks over four weeks at a dose of 200 mg.

Although the exact dosage will be determined on a drug-by-drug basis, in most cases, some generalizations regarding the dosage can be made. The daily dosage regimen for an adult human patient may be, for example, an oral dose of between 0.1 mg and 500 mg, preferably between 1 mg and 250 mg, e.g. 5 to 200 mg or an intravenous, subcutaneous, or intramuscular dose of each ingredient between 0.01 mg and 100 mg, for example between 0.1 mg and 60 mg, e.g. 1 to 40 mg of the pharmaceutical compositions of the present invention or a pharmaceutically acceptable salt thereof calculated as the free base, the composition being administered at a frequency dependent on its pharmacokinetics, e.g., 1 to 4 times per day. Alternatively the compositions of the invention may be administered by continuous intravenous infusion, preferably at a dose of each ingredient up to 400 mg per day. Thus, the total daily dosage by oral administration will typically be in the range 1 to 2000 mg and the total daily dosage by parenteral administration will typically be in the range 0.1 to 400 mg. Suitably the compounds will be administered for a period of continuous therapy, for example for a week or more, or for months or years, depending on the progress of the disease and the success of the treatment.

Dosage amount and interval may be adjusted individually to provide plasma levels of the active moiety which are sufficient to maintain the desired antiproliferative effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction; the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

EXAMPLES

Example 1

Expression of ODC, AdoMetDC, and MYCN in NB Cells

To characterize the NB cell lines LAN-1 and NMB-7 it was verified the presence of ODC, AdoMetDC, and MYCN at the RNA level using RT-PCR. Total RNA was isolated from subconfluent monolayer cell cultures and equal amounts of RNA were reverse-transcribed into cDNA and then analyzed by PCR using specific DNA primers. β-actin was included as a normalization standard. ODC, AdoMetDC, and MYCN RNAs were expressed in both cell lines as indicated by the PCR products of expected size at 400 bp, 450 bp, and 220 bp, respectively (FIG. 3a). The data are representative of similar results from three independent experiments. Each sample was measured in duplicate and data represent the mean of three independent experiments±SD. Specific enzyme activities are expressed as pmol $CO_2$/30 min/mg protein. These results confirm that LAN-1 and NMB-7 cells produce mRNA for both target enzymes and that both cell lines are of the MYCN-amplified NB subtype.

To determine the presence of ODC, AdoMetDC, and MYCN at the protein level, cell lysates containing equal amounts of protein were analyzed by Western blotting. ODC (53 kDa) and processed AdoMetDC α chain (31 kDa) proteins were detected at the expected size in LAN-1 and NMB-7 cells (FIG. 3b, left and middle panel), using an ODC-specific antibody and an AdoMetDC-recognizing rabbit serum, respectively. Because the latter interacted with several other proteins, it was verified the presence of AdoMetDC in LAN-1 cells treated with 5 mM DFMO and 10 μM SAM486A. The treatment of cells with both polyamine inhibitors for 3 days strongly induced AdoMetDC protein expression as indicated by an increase of the 31 kDa band, while the intensity of a second band at 75 kDa did not change (FIG. 3c). The MYCN protein (67 kDa) was also strongly expressed in LAN-1 and NMB-7 cells (FIG. 3b, right panel).

The presence and functionality of ODC and AdoMetDC was further demonstrated by measuring their respective enzyme activities in lysates of LAN-1 and NMB-7 cells harvested at early (day 1), mid (day 2), and late (day 3) log phase. As shown in FIG. 3d (ODC) and FIG. 3e (AdoMetDC), enzyme activities were detected in both cell lines. Specific activities were highest during early-to-mid log growth and proliferation phase with a marked decline in activity on day 3. Protein concentrations from cell lysates on days 1, 2, and 3 indicated logarithmic cell growth and proliferation (not shown). These results together clearly show that 1) mRNAs for ODC, AdoMetDC, and MYCN are present in LAN-1 and NMB-7 cells, 2) mRNAs are properly translated into proteins, and 3) ODC and AdoMetDC are functionally active enzymes.

Example 2

Effects of DFMO and SAM486A on ODC and AdoMetDC Activities, and Polyamine Pools The effects of DFMO and SAM486A on enzymatic activities of ODC and AdoMetDC in inhibitor-treated cells was determined. Cell lines LAN-1 and NMB-7 were left untreated (control) or treated with 5 mM DFMO, 10 µM SAM486A or the combination of both inhibitors for 2 days (mid-log phase) and enzyme activities were measured in cell lysates. In comparison with untreated cells, the ODC enzyme activity was lower after DFMO treatment and was further decreased by combined inhibitor treatment, while SAM486A alone increased ODC activity (Table 2).

TABLE 2

Effects of polyamine inhibitors on ODC and AdoMetDC activities in human neuroblastoma cells

| CELL LINE | TREATMENT[A] | SPECIFIC ENZYME ACTIVITIES (% OF CONTROL)[B] | |
|---|---|---|---|
| | | ODC | ADOMETDC |
| LAN-1 | Control | 100 ± 8 | 100 ± 12 |
| | DFMO | 26 ± 2 | 689 ± 94 |
| | SAM486A | 240 ± 27 | 169 ± 9 |
| | DFMO/SAM486A | 22 ± 2 | 490 ± 46 |
| NMB-7 | Control | 100 ± 11 | 100 ± 21 |
| | DFMO | 25 ± 8 | 582 ± 67 |
| | SAM486A | 251 ± 42 | 200 ± 16 |
| | DFMO/SAM486A | 23 ± 1 | 552 ± 64 |

[A]DFMO = 5 mM; SAM486A = 10 µM. Cells were analyzed 2 days after treatments.
[B]Values are presented as percentage (%) of specific enzyme activities (pmol $CO_2$/30 min/mg protein) relative to untreated control cells. Each sample was measured in duplicate and data represent the mean of three independent experiments ± SD.

Preincubation of extracts from untreated or DFMO-treated cells with 100 µM DFMO resulted in a complete loss of ODC activity (data not shown), indicating that the residual ODC activity represents a new steady state in the presence of the inhibitor rather than DFMO-resistant ODC protein. Under identical experimental conditions, AdoMetDC activity was determined. In contrast to ODC, it was found that treatment with DFMO, SAM486A or the combination of both inhibitors increased AdoMetDC activity (Table 2). SAM486A acts as a competitive inhibitor of AdoMetDC in the cell and is capable of stabilizing the enzyme, as shown in FIG. 3c. Therefore, AdoMetDC activity is elevated in the in vitro assay of SAM486A-treated cells because dilution of the cellular contents to prepare the cytosolic lysate reduces the concentration of SAM486A below the level necessary for inhibition and reveals the stabilization of the enzyme. Sequential dilution and concentration of cell lysates to remove the residual inhibitor further increased the measured AdoMetDC activity nearly 100-fold in SAM486A-treated cells (not shown). This contrasts with the irreversible inhibition of ODC by the suicide inhibitor DFMO, which is readily apparent in the in vitro assay. The further increase in AdoMetDC activity observed in cells treated with DFMO is likely because the treatment of cells with DFMO is known to induce AdoMetDC.

To study the effects of inhibitors on intracellular polyamine pools, LAN-1 and NMB-7 cells were treated with DFMO, SAM486A, or both inhibitors combined, for 2 and 3 days (Table 1). Inhibition of ODC by DFMO decreased Put and Spd pools in both cell lines while Spm pools decreased only slightly. Inhibition of AdoMetDC with SAM486A dramatically increased Put levels in both cell lines, indicating an efficient blockade in the polyamine biosynthetic pathway between Put and Spd, and reduced Spd and Spm levels. Combined inhibition of both enzymes decreased polyamine pools to various degrees, and exogenous supplementation of Spd (10 µM) to cell cultures led to a substantial increase in Spd. These observations are comparable with trends seen in other cell types (Kramer et al., (2001) *Cancer Res*, 61, 7754-62; Kramer et al., (1989) *Biochem J*, 259, 325-31; Svensson et al., (1997) *Biochem J*, 322, 297-302, each of which is incorporated herein by reference in its entirety). In untreated control cells, the levels of Put and Spd decreased during exponential cell growth and proliferation (day 0 to day 3), which is also consistent with a decrease in ODC and AdoMetDC enzyme activities (FIGS. 3d and 3e). Spm levels decreased in untreated LAN-1 cells and remained the same in NMB-7 cells (Table 1).

Example 3

Effects of DFMO and SAM486A on Cell Growth and Proliferation and Morphology

To determine the effects of DFMO and SAM486A on the growth and proliferation of NB cells, LAN-1 and NMB-7 cells were exposed to 5 mM DFMO, 10 µM SAM486A or the combination of both inhibitors for 3 days, and the cell number was determined. The cells were grown in the absence (1) or presence of 5 mM DFMO (2), 10 µM SAM486A (3), 5 mM DFMO plus 10 µM SAM486A (4), and 5 mM DFMO plus 10 µM SAM486A, supplemented with 10 µM Spd (5) for 3 days. As depicted in FIG. 4a, LAN-1 and NMB-7 cell growth and proliferation slowed substantially, and the combination of both inhibitors led to near-total cessation of cell growth and proliferation after 3 days. Exogenous supplementation of cell cultures with Spd (10 µM) clearly alleviated the growth and proliferation-inhibitory effects, thus indicating that the inhibition of cell growth and proliferation is due to polyamine pool depletion. Identical treatment of cells with 0.5 mM DFMO and 1 µM SAM486A (alone, and in combinations) resulted in dose-dependent growth and proliferation inhibition (not shown). Moreover, it was shown that DFMO and SAM486A inhibited the growth and proliferation of several other NB cell lines including SK-N-SH, SH-SY5Y (both MYCN-non-amplified and p53 wild type), LAN-5, and IMR-32 (both MYCN-amplified and p53 wild type) in a dose-dependent manner (not shown). Cell numbers are expressed as percentage (%) of control cell growth and proliferation. Each sample was measured in duplicate and the data represent the mean of three separate determinations±SD.

The observed growth and proliferation inhibition of LAN-1 and NMB-7 cells was accompanied by dramatic alterations in cell morphology (FIG. 4b). After 3 days of treatment with 5 mM DFMO, the triangular-shaped LAN-1 cells changed into spindle-like cells with neurite-like extensions. Under identical treatment, NMB-7 cells formed large polynucleate cell aggregates with only very short extensions. Treatment of these two cell lines with 10 µM SAM486A resulted in similar cell aggregates, but in the absence of neurite-like extensions. The combination of both inhibitors led to a mixed-type cell morphology, and supplementation of these cells with Spd (10 µM) at the beginning of the experiment alleviated the inhibitor effects, producing normal, triangular-shaped cells comparable to untreated control cells.

Figure 5:
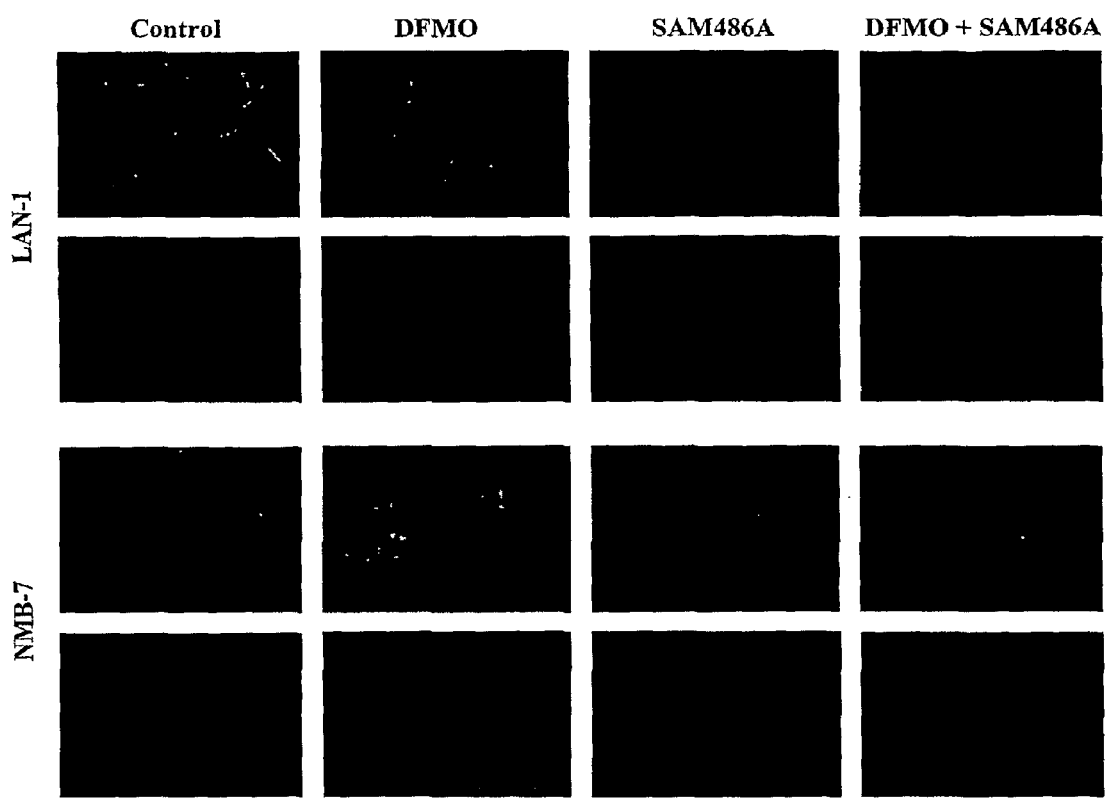
FIG. 5 contains representative fluorescence micrographs of the actin cytoskeleton and nuclei of human NB cells.

To further study these morphological changes, LAN-1 and NMB-7 cells were treated with 5 mM DFMO, 10 µM SAM486A or the combination of both inhibitors, and the actin cytoskeleton was visualized using phalloidin. Concomitant staining with DAPI allowed the visualization of cell nuclei. FIG. 5 shows representative fluorescence micrographs of the actin cytoskeleton and nuclei of human NB cells. LAN-1 and NMB-7 cells in the absence or presence of 5 mM DFMO, 10 μM SAM486A or the combination of both inhibitors, are shown 3 days after treatment. The actin cytoskeleton (red) was visualized with Texas Red-X phalloidin and cell nuclei (blue) were stained using 4',6-diamidino-2-phenylindole (DAPI). Strong cytoskeletal changes are visible after treatment with polyamine inhibitors. As shown in FIG. 5, the treatment with DFMO and/or SAM486A clearly disturbed the actin cytoskeleton in both cell lines. Furthermore, the DAPI-stained nuclei reveal the presence of polynucleate aggregates in both cell lines, which confirms that the large cell aggregates seen in FIG. 4b are indeed composites of several cells.

In summary, these data show that in NB cells, DFMO and SAM486A cause rapid growth and proliferation inhibition and induce morphological changes within 3 days. Similar effects were already apparent after 1-2 days (not shown). By comparison, the treatment of human melanoma cells (MALME-3) with polyamine inhibitors required more extensive incubation times (8-12 days) and led to less obvious rearrangements in cell structures (Kramer et al., (2001). *Cancer Res*, 61, 7754-62, which is incorporate herein by reference in its entirety). Furthermore, human ovarian cancer cells (SKOV-3), treated with DFMO or SAM486A, were not inhibited in their growth and proliferation and showed no visible changes in cell morphology.

Example 4

Prolonged Cell Growth and Proliferation Inhibition after Combined Treatment with DFMO and SAM496A To examine whether the combined treatment with DFMO and SAM486A produces NB cell populations, which loose their proliferative capacity permanently, LAN-1 and NMB-7 cells were either left untreated (control) or treated with 5 mM DFMO plus 10 μM SAM486A, and cell numbers were determined after 3 days (FIG. 6). FIG. 6 shows cell lines (a) LAN-1 and (b) NMB-7 in the absence (□) or the presence (●) of 5 mM DFMO plus 10 μM SAM486A. As expected, the growth and proliferation of cells treated with both inhibitors was strongly suppressed. On day 3, both untreated and treated cells were washed free of inhibitor by washing twice with PBS, reseeded in new medium (NM) (solid black arrow) without inhibitors at the starting cell density (dashed black arrow) and the experiment was continued for an additional 7 days. While the untreated LAN-1 and NMB-7 cells grew normally and reached similar cell densities after an additional 3 days (day 6 of the experiment), the initially treated LAN-1 and NMB-7 cells resumed proliferation only slowly and reached about 30% and 58% of control cell growth and proliferation, respectively, on day 10 of the experiment (FIG. 6). Cell numbers were determined using a hemocytometer and trypan blue reagent, and each data point is representative of three separate determinations±SD. This result indicates that the combined polyamine inhibitor treatment leads to sustained growth and proliferation arrest in both MYCN-amplified NB cell lines as, even after removal of inhibitors, their proliferative capacity is slowly and only partially restored. Similar experiments using DFMO and SAM486A individually revealed that the sustained growth and proliferation arrest was primarily due to the action of DFMO and not SAM486A (not shown).

Example 5

Effects of DFMO and SAM486A on Cell Cycle Distribution

Depletion of polyamines has previously been shown to cause $G_1$ cell cycle arrest in cancer cells. To investigate whether the observed growth and proliferation inhibition of NB cells is due to interference with cell cycle kinetics, LAN-1 and NMB-7 cells were treated with 5 mM DFMO, 10 μM SAM486A or the combination of both inhibitors, harvested, and stained with propidium iodide on days 2 and 3 of the experiment. As shown in Table 3, both inhibitors individually produced changes in the cell cycle distribution at days 2 and 3 of the experiment as indicated by the accumulation of cells in $G_1$ and a reduction of cells in S phase and in $G_2/M$ phase. This profile, which is typical for cell cycle arrest at $G_1$, was enhanced by the combination of both inhibitors, with the majority of cells in $G_1$ (~71-73%), a reduced number of cells in S phase (~20-28%), and a small portion in $G_2/M$ (~2-7%). Co-treatment with both inhibitors plus Spd (10 μM) prevented $G_1$ arrest (Table 3), which is in agreement with the growth and proliferation inhibition data shown in FIG. 4. The polyamine depletion-induced $G_1$ cell cycle arrest did not involve apoptosis as judged by (i) the absence of typical morphological changes such as nuclear condensation, membrane blebbing, and loss of cell adherence (FIGS. 4 and 5), (ii) the absence of PARP cleavage (not shown), and (iii) the lack of an apoptosis-associated $G_1$ sub-peak (Table 3).

TABLE 3

Effects of polyamine inhibitors on cell cycle phase distribution in human neuroblastoma cells

| CELL LINE | TREATMENT[A] | TIME (D) | CELL CYCLE (% TOTAL CELLS) | | | HISTOGRAM (FIG. 9) |
|---|---|---|---|---|---|---|
| | | | G1 | S | G2/M | |
| LAN-1 | Control | 0 | 50.0 ± 5.1 | 38.1 ± 8.0 | 11.9 ± 4.3 | |
| | Control | 2 | 47.9 ± 2.8 | 45.8 ± 2.7 | 6.3 ± 0.9 | FIG. 9a |
| | DFMO | 2 | 62.1 ± 10.4 | 26.4 ± 7.5 | 11.5 ± 3.0 | |
| | SAM486A | 2 | 58.7 ± 8.3 | 31.7 ± 6.8 | 9.6 ± 3.2 | |
| | DFMO/SAM486A | 2 | 73.4 ± 5.6 | 19.5 ± 4.9 | 7.1 ± 2.5 | FIG. 9b |
| | DFMO/SAM486A/Spd | 2 | 45.6 ± 4.8 | 45.9 ± 4.1 | 8.5 ± 0.8 | FIG. 9c |
| | Control | 3 | 52.0 ± 3.6 | 37.7 ± 4.5 | 10.4 ± 2.0 | |
| | DFMO | 3 | 63.1 ± 12.2 | 30.8 ± 8.2 | 6.2 ± 4.1 | |
| | SAM486A | 3 | 53.3 ± 5.1 | 37.4 ± 3.5 | 9.3 ± 2.0 | |
| | DFMO/SAM486A | 3 | 70.5 ± 9.6 | 25.5 ± 6.0 | 4.1 ± 3.5 | |
| | DFMO/SAM486A/Spd | 3 | 56.7 ± 5.9 | 34.3 ± 5.6 | 9.0 ± 0.4 | |

TABLE 3-continued

Effects of polyamine inhibitors on cell cycle phase distribution in human neuroblastoma cells

| CELL LINE | TREATMENT[A] | TIME (D) | CELL CYCLE (% TOTAL CELLS) | | | HISTOGRAM (FIG. 9) |
|---|---|---|---|---|---|---|
| | | | G1 | S | G2/M | |
| NMB-7 | Control | 0 | 45.0 ± 4.0 | 41.5 ± 3.3 | 13.5 ± 0.9 | |
| | Control | 2 | 47.0 ± 3.7 | 41.5 ± 3.9 | 11.5 ± 0.4 | FIG. 9d |
| | DFMO | 2 | 60.3 ± 3.9 | 31.3 ± 6.5 | 8.4 ± 2.9 | |
| | SAM486A | 2 | 54.1 ± 4.3 | 36.6 ± 6.0 | 9.3 ± 3.2 | |
| | DFMO/SAM486A | 2 | 71.6 ± 3.5 | 21.7 ± 2.6 | 6.7 ± 2.4 | FIG. 9e |
| | DFMO/SAM486A/Spd | 2 | 45.7 ± 6.6 | 45.7 ± 6.1 | 8.7 ± 2.8 | FIG. 9f |
| | Control | 3 | 56.7 ± 6.4 | 35.7 ± 7.3 | 7.6 ± 1.0 | |
| | DFMO | 3 | 58.8 ± 2.6 | 31.0 ± 6.3 | 10.2 ± 3.9 | |
| | SAM486A | 3 | 56.4 ± 6.5 | 35.2 ± 7.0 | 8.5 ± 1.4 | |
| | DFMO/SAM486A | 3 | 69.2 ± 4.1 | 28.4 ± 2.6 | 2.4 ± 2.3 | |
| | DFMO/SAM486A/Spd | 3 | 61.0 ± 10.1 | 31.9 ± 9.0 | 7.1 ± 1.1 | |

[A]DFMO = 5 mM; SAM486A = 10 µM; Spd = 10 µM.
[B]Data represent mean values from three separate experiments ± SD.

Example 6

Strong and Rapid Changes in Cell Cycle Regulatory Proteins p27$^{Kip1}$, Rb, and MYCN To this end, our data showed that the treatment of LAN-1 and NMB-7 cells with DFMO and/or SAM486A inhibits polyamine-dependent cell growth and proliferation and causes G$_1$ cell cycle arrest, and these effects could be largely prevented by the addition of Spd. To further investigate the mechanism that regulates G$_1$ arrest in LAN-1 and NMB-7 cells, and to define the changes in associated protein responses, the cell cycle-related proteins p21$^{Waf1/Cip1}$, p27$^{Kip1}$, p53, Rb, and MYCN in NB cell lysates were studied. Cells were analyzed on days 1, 2, and 3. Equal amounts of total protein were loaded in all experiments. Proteins were scanned and the ratio of hypophosphorylated Rb (pRb) (lower band):hyperphosphorylated Rb (ppRb) (upper band) was calculated (b). MYCN bands were quantified and normalized relative to β-actin. Values are presented as percentage (%) of controls of day 1, 2 or 3. (c). The data are representative of at least three independent experiments.

It was found that LAN-1 and NMB-7 cells treated with 5 mM DFMO increased endogenous levels of cdk inhibitor protein p27$^{Kip1}$ relative to untreated control cells after 2 days of treatment. This effect was enhanced on day 3 of the experiment and was further increased in the presence of both inhibitors (FIG. 7a). By comparison, treatment with 10 µM SAM486A alone did not alter p27$^{Kip1}$ levels. The result suggests that p27$^{Kip1}$ plays a role in the observed G$_1$ cell cycle arrest in NB cells (Table 3), and that this effect is primarily due to the action of DFMO, and not SAM486A. To test for the presence of the cdk inhibitor protein p21$^{Waf1/Cip1}$, identical experiments were conducted, but the protein could not be detected (not shown). Low levels of p21$^{Waf1/Cip1}$ in NB cells have been previously described (McKenzie et al., (2003). Cancer Res, 63, 3840-4, which is incorporated herein by reference in its entirety). Similarly, the tumor suppressor protein p53 was not detected (not shown), which is in agreement with previous findings that cell lines LAN-1 and NMB-7 are p53 deficient. In contrast, p53 was readily expressed in identical Western blot control experiments and detected by immunofluorescence using the p53 wild type cell line SK-N-SH (not shown).

The retinoblastoma protein Rb can be regulated through the action of p27$^{Kip1}$. Rb phosphorylation reduces the levels of functional Rb/E2F repressor complexes and activates E2F-responsive promoters important for moving the cell through the G$_1$/S phase of the cell cycle. To study the effects on Rb phosphorylation, LAN-1 and NMB-7 cells were treated with DFMO and/or SAM486A and analyzed on days 1, 2, and 3 using two phospho-specific Rb (p-Rb) antibodies as well as an antibody, which recognizes total Rb protein. As shown in FIG. 7b, Rb was phosphorylated at residue Ser795 and residues Ser807/811 in untreated LAN-1 and NMB-7 cells, while the treatment with DFMO or the combination of DFMO and SAM486A resulted in strong hypophosphorylation of Rb on days 2 and 3 of the experiment. The effect of SAM486A alone was much less pronounced. Rb hypophosphorylation was further confirmed with total Rb showing a visible mobility shift from a hyperphosphorylated form (upper band) to a hypophosphorylated form (lower band). The treatment with both inhibitors for 3 days completely dephosphorylated Rb and also decreased the total levels of Rb (FIG. 7b). Hypophosphorylation of Rb is a known consequence of p27$^{Kip1}$ induction, and this is in strong agreement with our findings. In summary, the results suggest that polyamine inhibitor-induced G$_1$ cell cycle arrest in MYCN-amplified NB cells is mediated by an increase in p27$^{Kip1}$ and subsequent hypophosphorylation of Rb.

Example 7

Treatment of a Patient having a Neuroblastoma with a Preferred Embodiment of the Invention A patient having a neuroblastoma is administered a combination therapy of DFMO, SAM486A, 13 cis retinoic acid and topotecan. The patient is administered an injection comprising 50 mg/m$^2$ of SAM486A, 15 mg/m$^2$ of 13 cis retinoic acid, and 25 mg/m$^2$ of topotecan. The patient is also administered an oral dose of 2 g/m$^2$ of DFMO dissolved in water. In some circumstances the DFMO dose is administered by injection in conjunction with the other therapeutic compounds. These compounds are administered once daily. In conjunction with this drug treatment, the patient is given a supply of meal replacement drinks/shakes that are essentially free of polyamines. The patient ingests these drinks/shakes three times a day in lieu of his or her normal diet. Generally, the patient is placed on this low polyamine diet one to ten days before the beginning of the administration of the therapeutic compounds in order to achieve polyamine titer reduction prior to the beginning of the administration of the therapeutic compounds.

Example 8

Treatment of a Patient having a Neuroblastoma with a Preferred Embodiment of the Invention A patient having a neuroblastoma is administered a combination therapy of DFMO, SAM486A, 13 cis retinoic acid and topotecan in a manner and dosage similar to that above. However, rather than administering each compound at the same time, the compounds are administered in series. For example, the patient is administered an injection comprising 50 mg/m$^2$ of SAM486A, 25 mg/m$^2$ of irinotecan and an oral dose of 2 g/m$^2$ of DFMO dissolved in water. In some circumstances the DFMO dose is administered by injection. This dosage continues for some period of time, anywhere from 1-3 weeks. Thereafter, 15 mg/m$^2$ of 13 cis retinoic acid is administered by injection, either in addition to, or in lieu of the combination of SAM486A, DFMO, and irinotecan. These compounds are administered once daily. In conjunction with this drug treatment, the patient is given a supply of meal replacement drinks/shakes that are essentially free of polyamines. The patient ingests these drinks/shakes three times a day in lieu of his or her normal diet. Generally, the patient is placed on this low polyamine diet one to ten days before the beginning of the administration of the therapeutic compounds in order to achieve polyamine titer reduction prior to the beginning of the administration of the therapeutic compounds.

Example 9

Treatment of a Patient having a Retinoblastoma with a Preferred Embodiment of the Invention A patient having a retinoblastoma is administered a combination therapy of DFMO, SAM486A, 13 cis retinoic acid and topotecan. The patient is administered an injection comprising 50 mg/m$^2$ of SAM486A, 15 mg/m$^2$ of 13 cis retinoic acid, and 25 mg/m$^2$ of topotecan. The patient is also administered an oral dose of 2 g/m$^2$ of DFMO dissolved in water. In some circumstances the DFMO dose is administered by injection in conjunction with the other therapeutic compounds. These compounds are administered once daily. In conjunction with this drug treatment, the patient is given a supply of meal replacement drinks/shakes that are essentially free of polyamines. The patient ingests these drinks/shakes three times a day in lieu of his or her normal diet. Generally, the patient is placed on this low polyamine diet one to ten days before the beginning of the administration of the therapeutic compounds in order to achieve polyamine titer reduction prior to the beginning of the administration of the therapeutic compounds. The administration of the compounds could also be done on an interval/intermittent basis as shown in Example 8.

Example 10

Treatment of a Patient having Breast Cancer with a Preferred Embodiment of the Invention A patient having breast cancer is administered a combination therapy of DFMO, SAM486A, fenretidine and irinotecan in a manner and dosage similar to that above. These compounds are administered once daily. In conjunction with this drug treatment, the patient is given a supply of meal replacement drinks/shakes that are essentially free of polyamines. The patient ingests these drinks/shakes three times a day in lieu of his or her normal diet. Generally, the patient is placed on this low polyamine diet one to ten days before the beginning of the administration of the therapeutic compounds in order to achieve polyamine titer reduction prior to the beginning of the administration of the therapeutic compounds. The administration of the compounds could also be done on an interval/intermittent basis as shown in Example 8.

Example 11

Treatment of a Patient having Breast Cancer with a Preferred Embodiment of the Invention A patient having breast cancer is administered a combination therapy of DFMO, SAM486A, fenretidine and irinotecan in a manner and dosage similar to that in Example 7. These compounds are administered once daily. The administration of the compounds could also be done on an interval/intermittent basis as shown in Example 8.

In conjunction with this drug treatment, the patient is provided dietary instructions. These instructions describe a diet and/or dietary factors that relate to polyamine levels. The instructions show the patient how to adopt a diet essentially free of polyamines. Generally, the patient is given these instructions one to ten days before the beginning of the administration of the therapeutic compounds in order to achieve polyamine titer reduction prior to the beginning of the administration of the therapeutic compounds. However, these instructions may also be given to the patient at the time of the first treatment.

Example 12

Treatment of a Patient having a Neuroblastoma with a Preferred Embodiment of the Invention A patient having a neuroblastoma is administered a combination therapy of DFMO, SAM486A, 13 cis retinoic acid and paclitaxel in an appropriate dosage and in a manner similar to that in Example 7. These compounds are administered once daily. The administration of the compounds could also be done on an interval/intermittent basis as shown in Example 8. In conjunction with this drug treatment, the patient is given a supply of meal replacement drinks/shakes that are essentially free of polyamines. The patient ingests these drinks/shakes three times a day in lieu of his or her normal diet. Generally, the patient is placed on this low polyamine diet one to ten days before the beginning of the administration of the therapeutic compounds in order to achieve polyamine titer reduction prior to the beginning of the administration of the therapeutic compounds.

Example 13

Treatment of a Patient having Neuroblastoma with a Preferred Embodiment of the Invention A patient having a neuroblastoma is administered a combination therapy of DFMO, SAM486A, 13 cis retinoic acid and DENSpm in an appropriate dosage and in a manner similar to that in Example 7. DFMO, SAM486A and 13 cis retinoic acid are administered once daily. The DENSpm is administered on a cycle, whereby an appropriate dose is administered intravenously for five consecutive days every 21 days. The administration of the other compounds could also be done on an interval/intermittent basis as shown in Example 8. In conjunction with this drug treatment, the patient is given a supply of meal replacement drinks/shakes that are essentially free of polyamines. The patient ingests these drinks/shakes three times a day in lieu of his or her normal diet. Generally, the patient is placed on this low polyamine diet one to ten days before the beginning of the administration of the therapeutic compounds in order to achieve polyamine titer reduction prior to the beginning of the administration of the therapeutic compounds.

Materials and Methods:

Cell Lines and Treatment of Cultured Cells

Human NB cell lines were provided by Dr. Robert Seeger (LAN-1; University of California, Los Angeles, Calif.), Dr. Nai-Kong Cheung (NMB-7; Memorial Sloan-Kettering Cancer Center, NY), and the American Type Culture Collection (SK-N-SH; ATCC, Manassas, Va.). Cells were maintained in RPMI 1640 (Biosource, Rockeville, Md.) containing 10% heat-inactivated fetal bovine serum (FBS) (Invitrogen, Carlsbad, Calif.), penicillin (100 IU/ml) and streptomycin (100 µg/ml). If cells were treated with exogenous Spd, 1 mM of aminoguanidine was included as an inhibitor of serum polyamine oxidation. Cells in early log-phase were seeded 2-3 hours before treatment with 5 mM DFMO and/or 10 µM SAM486A and analyzed after 1, 2 and/or 3 days. For growth and proliferation inhibition, polyamine pool, and cell cycle studies, 10 µM Spd was added together with inhibitors, and cells were assayed on days 2 and/or 3.

ODC and AdoMetDC Activity Assays

ODC and AdoMetDC enzyme activities were determined using a standard assay known in the art. In brief, NB cells were washed twice with ice-cold PBS and harvested in 50 mM sodium phosphate buffer (pH 7.2), 0.1 mM EDTA, 2.5 mM DTT, supplemented with 1× protease inhibitor cocktail (Roche Molecular Biochemicals, Indianapolis, Ind.). For the measurement of AdoMetDC activity, cells were harvested in the above buffer supplemented with 2.5 mM Put. Cells were lysed by three freeze/thaw cycles and cell lysates were prepared by centrifugation for 20 minutes at 14,000 rpm and 4° C. ODC activity was measured in a reaction mixture that contained 20 µM L-[1-$^{14}$C]ornithine (47.70 mCi/mmol; NEN Life Science Products, Boston, Mass.). AdoMetDC activity was assayed in a reaction mixture that contained 8.2 µM S-adenosyl-L-[carboxy-$^{14}$C]methionine (58.0-61.0 mCi/mmol; Amersham Biosciences, Piscataway, N.J.) and 140.1 µM cold S-adenosylmethionine. Extracts from untreated or DFMO-treated LAN-1 cells were incubated in 100 µM DFMO for 30 min at 37° C. prior to the ODC activity assay to test for DFMO-resistant ODC. Untreated or SAM486A-treated LAN-1 extracts were assayed for AdoMetDC activity after multiple rounds of sequential dilution with harvest buffer followed by concentration of the extract (Centricon YM-10, Millipore Corporation, Bedford, Mass.) to remove the inhibitor. This process resulted in an approximately 400-fold dilution of the residual inhibitor in the extract without a significant change in the overall protein concentration.

Polyamine Pool Analysis

Intracellular polyamines were extracted from cell pellets by a method known in the art. In brief, cells were washed and centrifuged. After sonication and centrifugation, 250 µl of supernatant, 100 µl of saturated sodium carbonate, and 300 µl of 25 mg/ml dansyl chloride (5-dimethylamino-naphthalene-1-sulfonyl chloride) (Fluka, Switzerland) were mixed and analyzed via reverse phase HPLC using a C18 reverse-phase analytical column (Waters, Milford, Mass.). The effluent from the column was monitored at 510 nm (excitation at 330 nm). Polyamine levels were determined using appropriate standards. The samples were normalized in 0.2 N sodium hydroxide and the amount of total protein per sample was measured using the Bradford assay (70). Polyamine levels are expressed as nmol per mg of total cellular protein.

What is claimed is:

1. A method of treating N-MYC amplified and overexpressed tumors in a mammal, comprising: administering to said mammal a composition comprising therapeutically effective amounts of alpha-difluoromethylornithine (DFMO) and etoposide, wherein administration of the composition results in inhibition of abnormal cell proliferation, wherein the N-MYC amplified and overexpressed tumor is a neuroblastoma tumor.

2. The method of claim 1, further comprising administration of a retinoid.

3. The method of claim 2, wherein the retinoid is fenritidine or 13 cis retinoic acid.

4. The method of claim 1 further comprising putting the mammal on a low-polyamine diet.

5. The method of claim 4 wherein said putting the mammal on a low-polyamine diet comprises providing the mammal with dietary instructions.

6. The method of claim 5 wherein said putting the mammal on a low-polyamine diet comprises providing the mammal with low polyamine meal replacements.

* * * * *